US010278962B2

United States Patent
Nan et al.

(10) Patent No.: US 10,278,962 B2
(45) Date of Patent: May 7, 2019

(54) TRICYCLIC ANALOGUES, PREPARATION METHOD AND USES THEREOF

(71) Applicant: SHANGHAI INSTITUTE OF MATERIA MEDICA, CHINESE ACADEMY OF SCIENCES, Pudong, Shanghai (CN)

(72) Inventors: Fajun Nan, Shanghai (CN); Boliang Li, Shanghai (CN); Yang Zhan, Shanghai (CN); Xiaowei Zhang, Shanghai (CN); Ying Xiong, Shanghai (CN); Xichan Hu, Shanghai (CN); Yangming Zhang, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 15/556,932

(22) PCT Filed: Mar. 3, 2016

(86) PCT No.: PCT/CN2016/075391
§ 371 (c)(1),
(2) Date: Sep. 8, 2017

(87) PCT Pub. No.: WO2016/145994
PCT Pub. Date: Sep. 22, 2016

(65) Prior Publication Data
US 2018/0064696 A1 Mar. 8, 2018

(30) Foreign Application Priority Data
Mar. 19, 2015 (CN) .......................... 2015 1 0121662

(51) Int. Cl.
*A61K 31/4433* (2006.01)
*C07D 493/04* (2006.01)
*A61K 31/352* (2006.01)
*C07B 37/04* (2006.01)
*C07B 49/00* (2006.01)

(52) U.S. Cl.
CPC ........ *A61K 31/4433* (2013.01); *A61K 31/352* (2013.01); *C07D 493/04* (2013.01); *C07B 37/04* (2013.01); *C07B 49/00* (2013.01)

(58) Field of Classification Search
CPC ........................... C07D 493/04; A61K 31/4453
See application file for complete search history.

(56) References Cited

U.S. PATENT DOCUMENTS

| 5,958,970 A * | 9/1999 | Hua ...................... C07C 69/738 |
| | | 514/224.5 |
| 6,916,824 B1 * | 7/2005 | Hua ..................... A61K 9/0048 |
| | | 514/291 |
| 7,935,726 B1 | 5/2011 | Hua |
| 9,896,456 B2 * | 2/2018 | Tomoda ............... A61K 31/366 |

OTHER PUBLICATIONS

Hua et al (1998):STN International, HCAPLUS database (Columbus, Ohio), Accession No. 1998: 618823.*
Newell et al (1998):STN International, HCAPLUS database (Columbus, Ohio), Accession No. 1998: 86353.*
International Search Report, International Preliminary Report on Patentability and Written Opinion, issued in International Patent Application No. PCT/CN2016/075391, dated Jun. 2016.
Lewis, S. et al. Synthesis and Evaluation of Novel Aldose Reductase Inhibitors: Effects on Lens Protein Kinase Cγ, Molecular Vision, Jul. 18, 2001, vol. 7, pp. 164-171.
Zehnder, Luke R, et al. "Lewis Acid Mediated Condensation Reactions of @a,@b-Unsaturated Acids with 4-Hydroxy-2-Pyrones. A Concise Structural Assignment of Fleischmann's @a,@a-Bispyrone and Praill's @a,@c-Bispyrone", Tetrahedron Letters, Dec. 31, 2000, vol. 41, Issue 12. (Abstract).

* cited by examiner

*Primary Examiner* — Golam M Shameem
(74) *Attorney, Agent, or Firm* — Ping Wang; Morris, Manning & Martin, LLP

(57) ABSTRACT

The present invention relates to a series of analogs of natural product Pyripyropene A represented by general formula I and a preparation method and use thereof. More particularly, the present invention relates to analogs of the natural product Pyripyropene A, a preparation method and use thereof as the acyl-CoA:cholesterol acyltransferase 2 (ACAT2) inhibitors for the treatment of cardiovascular diseases such as atherosclerosis and the like.

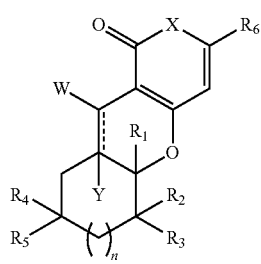

6 Claims, No Drawings

US 10,278,962 B2

TRICYCLIC ANALOGUES, PREPARATION METHOD AND USES THEREOF

TECHNICAL FIELD

The present invention belongs to the field of pharmaceutical chemistry, and relates to a series of analogues of natural product Pyripyropene A, and a preparation method and use thereof. More particularly, the present invention relates to analogues of the natural product Pyripyropene A, a preparation method and the use thereof as inhibitors of acyl-CoA: cholesterol acyltransferase 2 (ACAT2) for the treatment of cardiovascular diseases such as atherosclerosis and the like.

BACKGROUND ART

Cholesterol, which plays a very important role in organisms, is essential for the survival of all animal cells. Under normal physiological conditions, the cholesterol in higher biological cells is maintained at a level of a fairly narrow range. When cholesterol concentration is too high or too low, the normal life process will be affected, even serious lesions will occur. Cells maintain a normal cholesterol concentration mainly by regulating the balance between various pathways such as the synthesis, absorption, esterification, and outflow of cholesterol. Among them, the esterification of cholesterol, which is catalyzed by acyl-CoA: cholesterol acyltransferase (ACAT), plays a very important role in the balance of cholesterol metabolism both at the cell level and at the individual level. ACAT is the only enzyme in cells that synthesizes cholesteryl esters—catalyzing the formation of cholesteryl esters by connecting free cholesterol with fatty acid long chains.

ACAT is a membrane-bound protein located on the rough endoplasmic reticulum of the tissue cells. Two subtypes were found: ACAT1 and ACAT2. Both of them have different locations and distribution. ACAT1 almost exists in various tissues and cells, and regulates cholesterol levels in tissues such as brain, macrophages and adrenal glands. In contrast, ACAT2, which is expressed specifically in liver and small intestine cells, is responsible for the esterification and synthesis of cholesterol in liver and small intestine. It has long been recognized that ACAT is closely associated to the occurrence of atherosclerosis. Thus, inhibition of ACAT can not only attenuate the absorption of cholesterol by small intestine, but also inhibit the formation of multiple types of foam cells, including macrophage source, and thus it is a very important target for the treatment of cardiovascular disease.

Currently known ACAT inhibitors are mainly classified as follows: a. synthetic inhibitors: including ureas, amides, and imidazoles; b. microbial inhibitors; c. natural plant inhibitors. However, until now none of the existing ACAT inhibitors has been developed into drugs because the selectivity of inhibitory activity for the two subtypes of ACAT has been ignored. Later, different conclusions were drawn when evaluating the effect on atherosclerosis by inhibiting ACAT1. One laboratory believed that the absence of ACAT1 can inhibit the occurrence of atherosclerosis; whereas the test results from another laboratory showed that the risk of atherosclerosis is greatly increased in the ACAT1-deficient mice. It has been found in the mice without ACAT2 that ACAT-2$^{-/-}$ mice had lower ability to absorb cholesterol and were resistant to calculus and food-induced hypercholesterolemia. Therefore, it is predicted that specific inhibition of ACAT1 will disrupt the balance of intracellular cholesterol metabolism, leading to cytotoxicity of cholesterol, which is not helpful for preventing the occurrence of atherosclerosis. And ACAT2 may be an effective target for the prevention of hyperlipidemia and atherosclerosis. Specific inhibition of ACAT2 will reduce absorption and transport of cholesterol, and will not affect intracellular cholesterol metabolism balance. In conclusion, it is very important to develop an inhibitor with high selectivity targeting ACAT2.

However, after retesting the discovered ACAT inhibitors, it was found that only Pyripyropene A has ACAT2-specific inhibitory activity. Pyripyropenes were extracted and obtained from the fermentation broth of microorganism *Aspergillus fumigates* FO-1289 by Satoshi Omura et al. in 1993. It is very difficult to obtain Pyripyropenes by isolation process from natural sources, since the process involves cumbersome procedures with low production. Besides, natural Pyripyropenes have the drawback in difficult preparation. For example, starting from carvone, the synthetic route has up to nineteen steps, many of which require very harsh reaction conditions, and the yield is very low. In order to find a novel ACAT2 inhibitor with higher inhibitory activity and better selectivity, the present inventor tried to simplify the structure of Pyripyropenes by removing the ring structure in the nucleus of Pyripyropenes, which perhaps is most complicated to synthesize in the preparing process, eliminating the two methylene groups and one corner methyl group in the leftmost ring, and retaining the key diacetyl structure unit, thereby obtaining a structurally-simplified target molecule with a whole new skeleton, whose structural complexity is greatly reduced and thus is easy to produce from the simple natural ingredient carvone. A class of tricyclic compounds of Pyripyropenes disclosed by the present invention is characterized in that, comparing with the natural product Pyripyropene A, the ACAT2 specific inhibitory activity of the compounds, which are obtained by removing the leftmost ring system, increases greatly. The invention discloses the effect of this structure on the activity and obtains a series of compounds with excellent properties. When compared with the natural product Pyripyropene A, these compounds are not only simple to synthesize, but also significantly better in the aspects of inhibitory activity of ACAT2 and selective inhibition of ACAT2. They are expected to be developed into novel ACAT2-targeting drugs for the treatment of cardiovascular diseases such as atherosclerosis and the like.

CONTENT OF THE INVENTION

An object of the present invention is to design and synthesize a class of novel and simplified analogues of Pyripyropene A, which can act as ACAT2 inhibitors, thereby exploring a new way for developing drugs for the treatment of cardiovascular diseases such as atherosclerosis and the like.

Another object of the present invention is to provide a method for preparing the analogues of Pyripyropene A as described above.

A further object of the present invention is to provide the use of the analogues of Pyripyropene A as described above.

The analogues of Pyripyropene A of the present invention have a structure represented by the following general formula (I):

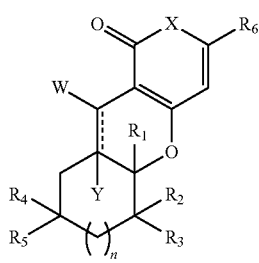

I wherein:

n=0, 1 or 2; preferably n=1;

$R_1$ is hydrogen or C1 to C6 alkyl; preferably, $R_1$ is hydrogen or methyl;

$R_2$ and $R_3$ are each independently hydrogen, hydroxy, C1 to C6 alkylcarbonyloxy group, C1 to C6 alkylcarbonylthio group, C1 to C6 alkylcarbonylamine group, 3- to 8-membered cycloalkylcarbonyloxy group, 3- to 8-membered cycloalkylcarbonylthio group, 3- to 8-membered cycloalkylcarbonylamine group, substituted or unsubstituted 5- to 8-membered arylcarbonyloxy group, substituted or unsubstituted heteroarylcarbonyloxy group, wherein the term of "substituted" means to be substituted with halogen, hydroxy, alkyl, alkoxy, amino, cyano, and preferably, $R_2$ and $R_3$ are each independently hydrogen, hydroxy, ethylcarbonyloxy group (i.e., acetoxy, —OAc) or para-cyano-substituted phenylcarbonyloxy group; more preferably, one of $R_2$ and $R_3$ is hydrogen and the other is selected from hydroxy, ethylcarbonyloxy groups (i.e., acetoxy, —OAc) or para-cyano-substituted phenylcarbonyloxy groups;

$R_4$ and $R_5$ are each independently hydrogen, hydroxy, C1 to C6 alkylcarbonyloxy group, C1 to C6 alkylcarbonylthio group, C1 to C6 alkylcarbonylamine group, 3- to 8-membered cycloalkylcarbonyloxy group, 3- to 8-membered cycloalkylcarbonylthio group, 3- to 8-membered cycloalkylcarbonylamine group,

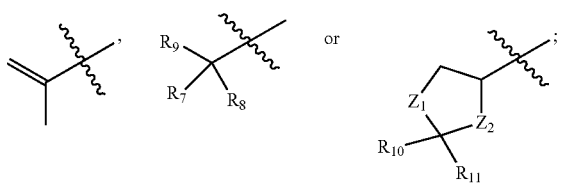

wherein $R_7$, $R_8$ and $R_9$ are each independently hydrogen, hydroxy, halogen, methyl, C1 to C6 alkylcarbonyloxy group, C1 to C6 alkylcarbonylthio group, C1 to C6 alkylcarbonylamine group, 3- to 8-membered cycloalkylcarbonyloxy group, 3- to 8-membered cycloalkylcarbonylthio group, 3- to 8-membered cycloalkylcarbonylamine group, C1 to C6 alkylcarbonyloxy methylene group, 3- to 8-membered cycloalkylcarbonyloxy methylene group, substituted or unsubstituted 5- to 8-membered heteroarylcarbonyloxy group, substituted or unsubstituted 5- to 8-membered heteroarylcarbonyloxymethylene group, substituted or unsubstituted 5- to 8-membered arylcarbonyloxy group, substituted or unsubstituted 5- to 8-membered arylcarbonyloxy methylene group, wherein the term of "substituted" means to be substituted with halogen, hydroxy, alkyl, alkoxy, amino, cyano; $Z_1$ and $Z_2$ are each independently hydrogen, oxygen atom, sulfur atom or amino group; $R_{10}$ and $R_{11}$ are each independently hydrogen, C1 to C6 alkyl, 3- to 8-membered cycloalkyl, substituted or unsubstituted 5- to 8-membered heteroaryl, substituted or unsubstituted 5- to 8-membered aryl, wherein the term of "substituted" means to be substituted with halogen, hydroxy, alkyl, alkoxy, amino, cyano; preferably, $R_4$ and $R_5$ are each independently hydrogen,

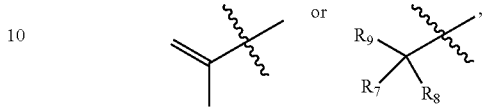

$R_7$, $R_8$ and $R_9$ are each independently hydrogen, hydroxy, halogen, methyl, C1 to C6 alkylcarbonyloxy group, substituted or unsubstituted phenylcarbonyloxy group, wherein the term of "substituted" means to be substituted with para cyano; and more preferably, one of $R_4$ and $R_5$ is hydrogen and the other is

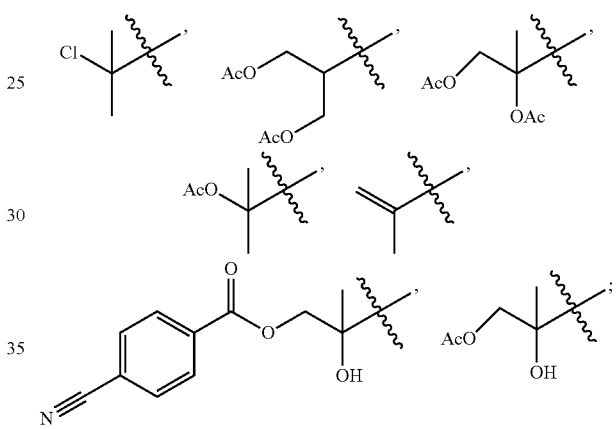

$R_6$ is unsubstituted or substituted C1 to C6 alkyl, unsubstituted or substituted C1 to C6 alkenyl, substituted or unsubstituted 5- to 8-membered heteroaryl, substituted or unsubstituted 5- to 8-membered aryl, substituted or unsubstituted 3- to 8-membered cycloalkyl, wherein the term of "substituted" means to be substituted with halogen, hydroxy, alkyl, alkoxy, amino, cyano; preferably, $R_6$ is substituted or unsubstituted 5- to 8-membered heteroaryl; more preferably, $R_6$ is a 3-pyridyl group;

X is an oxygen atom, a sulfur atom, an amino or a C1 to C6 alkyl; preferably, X is an oxygen atom;

Y is hydrogen;

W is hydrogen, hydroxy, halogen, oxo (=O), =N—OH, substituted or unsubstituted 5- to 8-membered aryl or heteroarylcarbonyloxy group, C1 to C6 alkylcarbonyloxy group or 3- to 8-membered cycloalkylcarbonyloxy group; preferably, W is hydroxy, oxo (=O) or para-halogen-substituted phenylcarbonyloxy;

==== represents a single bond or a double bond; preferably is a single bond.

In the present invention,

represents a linking site, unless otherwise indicated.

In a preferred embodiment of the present invention, Y is hydrogen, n=1, and ==== is a single bond, that is, the analogue of Pyripyropene A, represented by general formula (I), of the present invention have a structure represented by the following general formula (II):

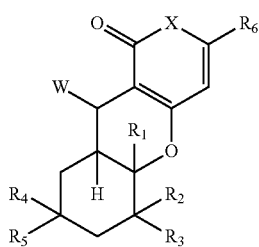

The definitions of the respective substituents in the general formula (II) are the same as those in general formula (I).

More preferably, Y is hydrogen, n=1, X is oxygen, $R_1$ is a methyl group, and ==== is a single bond, that is, the analogue of Pyripyropene A, represented by general formula (I), of the present invention have a structure represented by the following general formula (III):

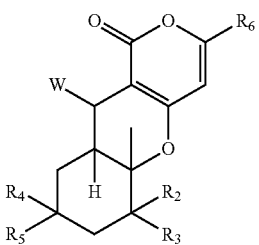

wherein in general formula (III), the definitions of the respective substituents are the same as those in general formula (I).

More preferably, Y is hydrogen, n=1, X is oxygen, $R_1$ is methyl, ==== is a single bond, $R_3$ and $R_5$ are hydrogen, and the absolute configuration of each chiral center is as follows: the configurations of W and Y are the same, the configurations of $R_2$, $R_4$ and $R_1$ are the absolute steric configurations represented by the following general formula (IV):

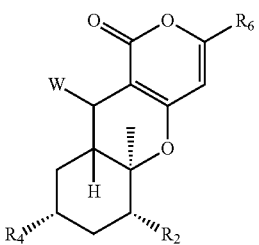

wherein in general formula (IV), the definitions of the respective substituents are the same as those in general formula (I).

In the specification, the term of "C1 to C6 alkyl" may be a straight or branched C1 to C6 alkyl group, specifically, may be methyl, ethyl, propyl, isopropyl, butyl, tert-butyl, isobutyl, pentyl, neopentyl or hexyl; preferably may be straight or branched C1 to C3 alkyl.

In the specification, the term of "5- to 8-membered heteroaryl" is a 5- to 8-membered ring aromatic group;

In the specification, the term of "5- to 8-membered cycloalkyl" is a cycloalkyl group having a 5- to 8-membered ring, specifically, may be cyclopropyl, cyclobutyl, cyclopentyl, cyclohexyl, cycloheptyl or cyclooctyl.

In the specification, the term of "C1 to C6 alkylcarbonyloxy group" is $C_nH_{2n+1}COO-$, and n is 1 to 6.

In the specification, the term of "C1 to C6 alkylcarbonylthio group" is $C_nH_{2n+1}COS-$, and n is 1 to 6.

In the specification, die term of "C1 to C6 alkylcarbonylamine group" is $C_nH_{2n+1}CONH-$ and n is 1 to 6.

In the specification, the term of "3- to 8-membered cycloalkylcarbonyloxy group" is —OCO— 3 to 8-membered ring.

In the specification, the term of "3- to 8-membered cycloalkylcarbonylthio group" is —SCO— 3 to 8-membered ring.

In the specification, the term of "3- to 8-membered cycloalkylcarbonylamine group" is —NCO— 3 to 8-membered ring.

In the specification, the term of "C1 to C6 alkylcarbonyloxy methylene" is $C_nH_{2n+1}COOCH_2-$, and n is 1 to 6.

In the specification, the term of "3- to 8-membered cycloalkylcarbonyloxy methylene" is —CH$_2$OCO— 3 to 8-membered ring.

In a more preferred embodiment of the present invention, the analogue of Pyripyropene A, represented by general formula (I), of the present invention are specifically as follows:

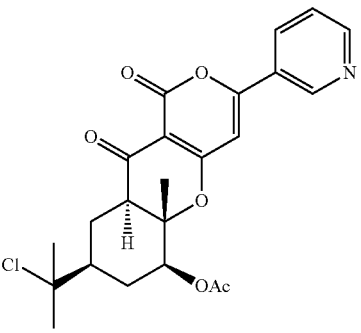

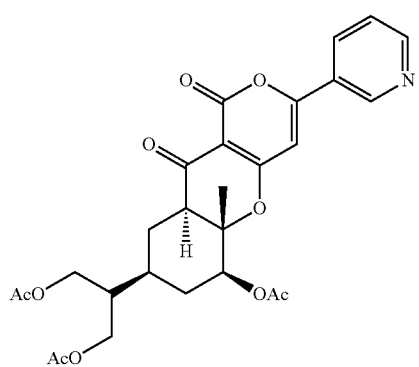

-continued
3
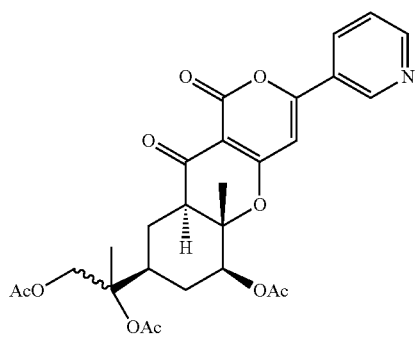
4
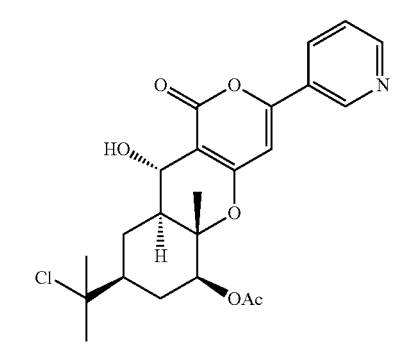
5
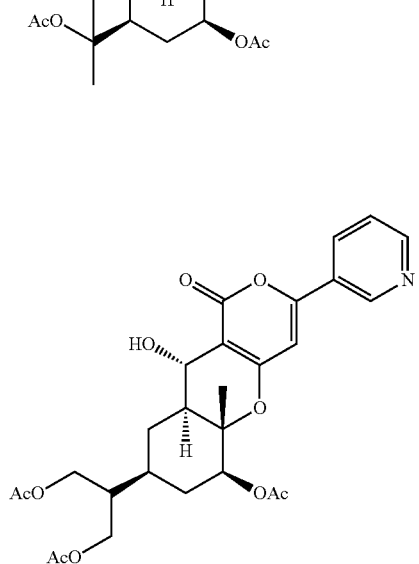
6
-continued
7
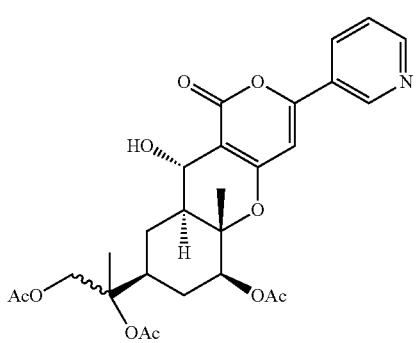
8
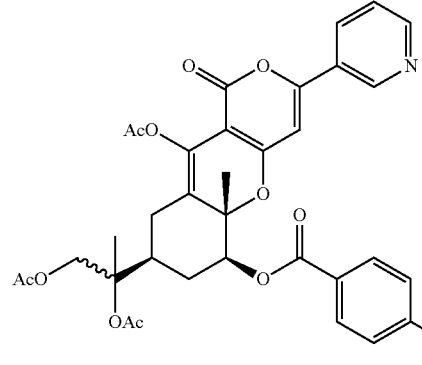
9
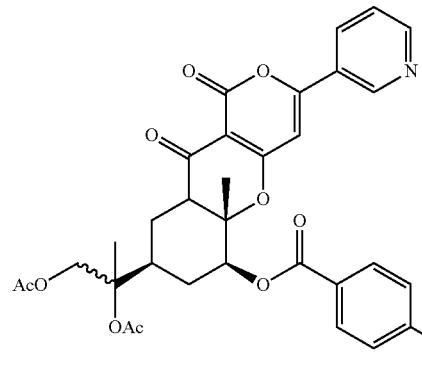
10
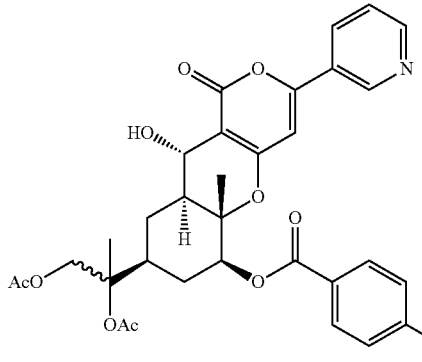

11
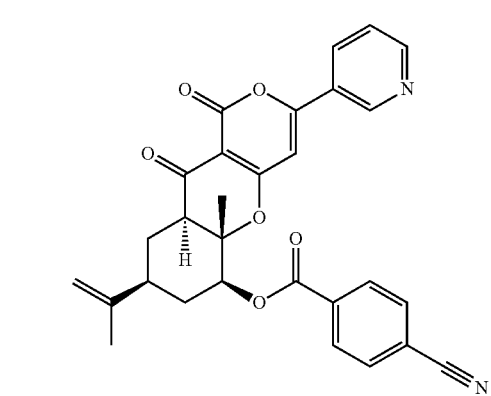
12
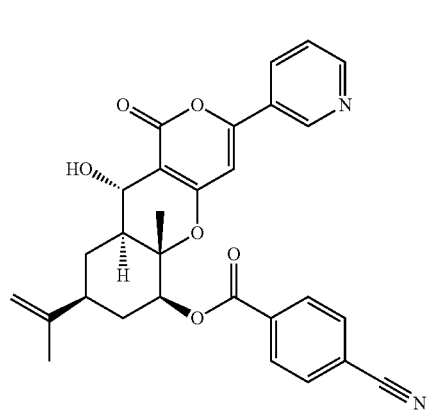
13
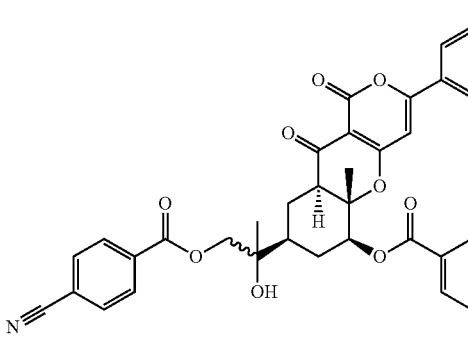
14
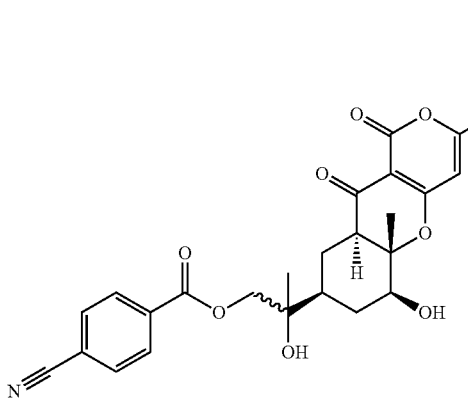
15
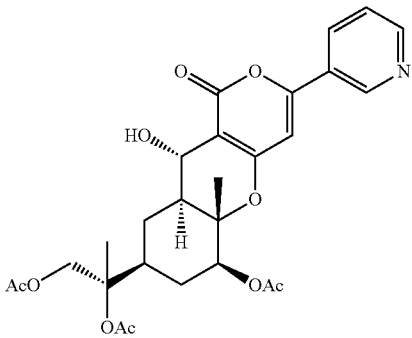
16
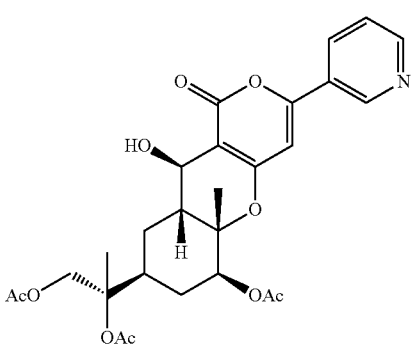
17
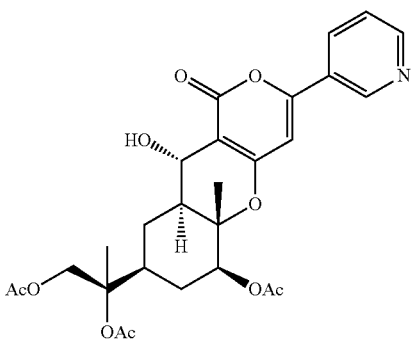
18
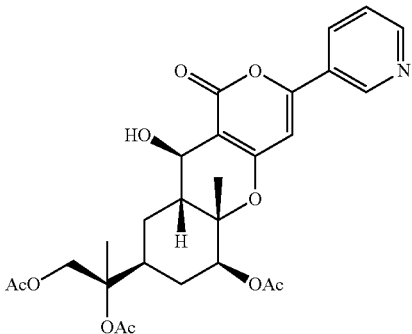

19
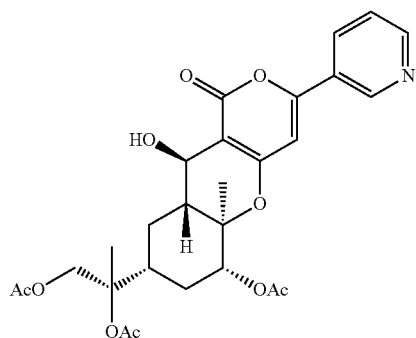
20
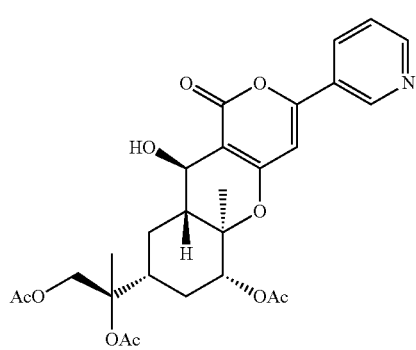
21
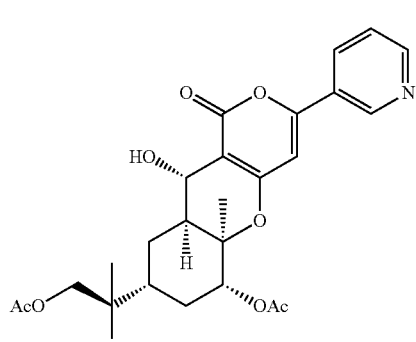
22
23
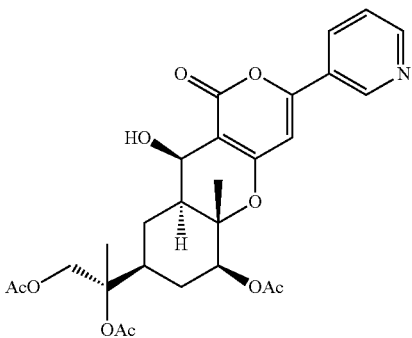
24
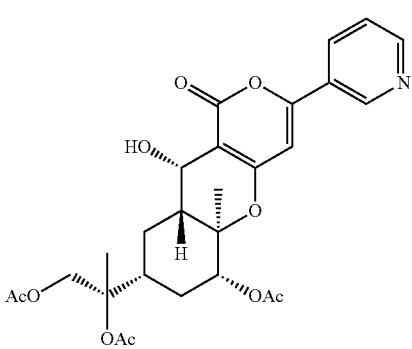
25
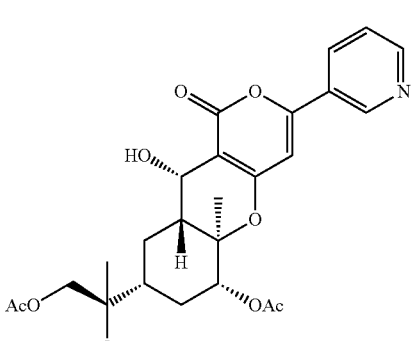
26

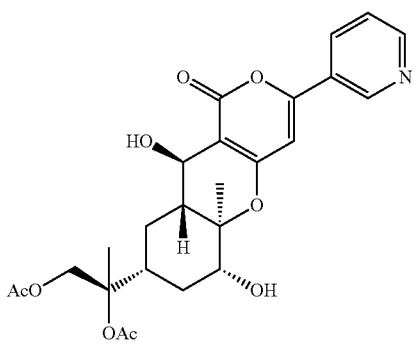
27
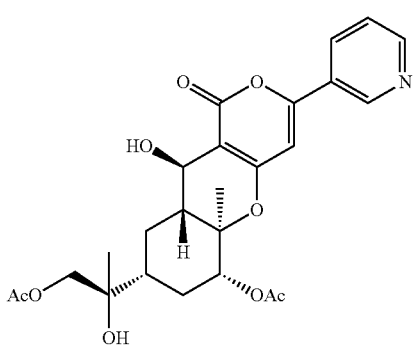
28
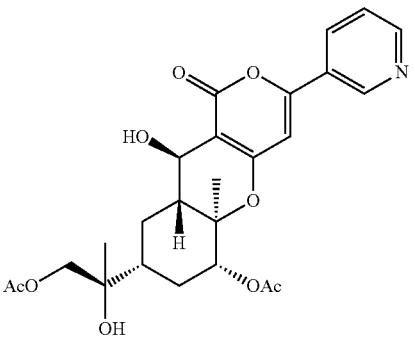
29
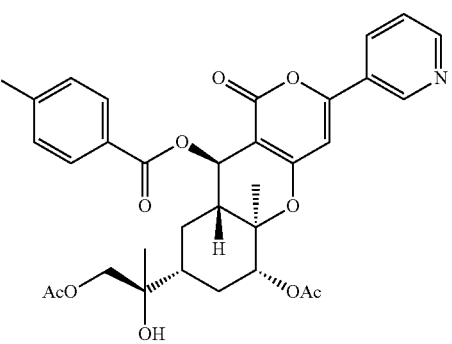
30
The present invention provides a method for preparing analogues of Pyripyropene A which are represented by general formula (I). The preparation method can be carried out by the following route:
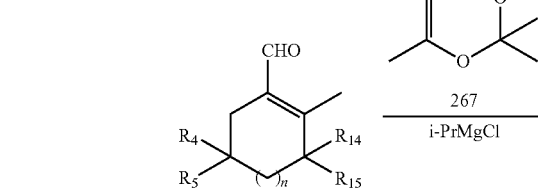
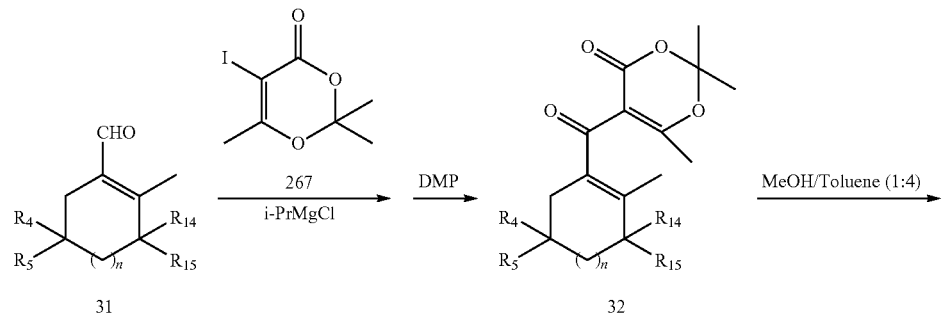
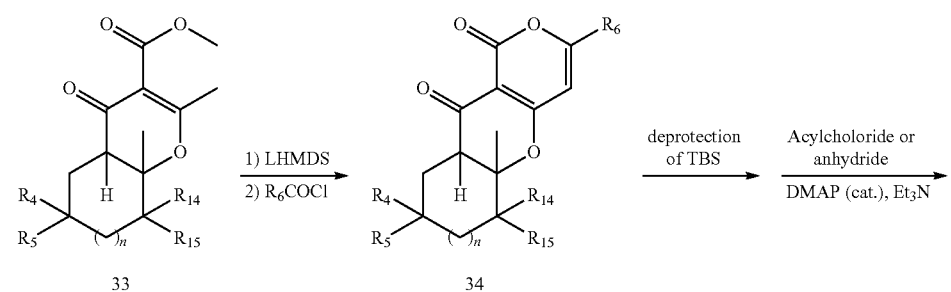

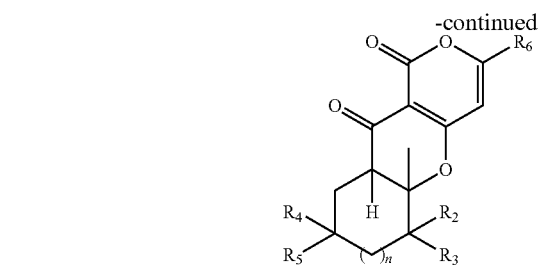
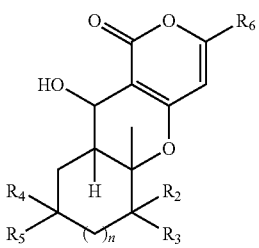

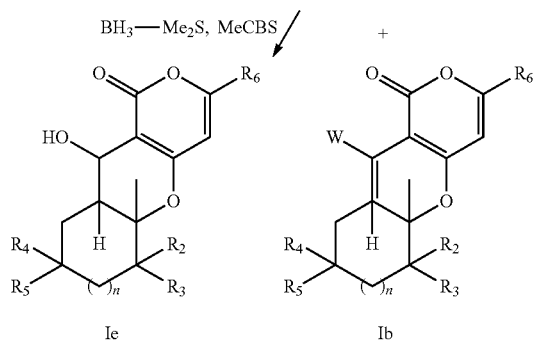
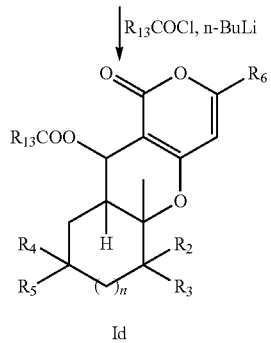

Specifically, the method comprises the following steps:

(1) compound 31 and compound 267 are subjected to coupling reaction together with isopropyl Grignard reagent in THF and then oxidized to form compound 32;

(2) compound 32 is subjected to a solvolysis reaction to give compound 33;

(3) compound 33 is enolized with LHMDS and then undergoes a C-acylation ring-closing reaction with acyl chloride having a different group ($R_6COCl$) to give compound 34;

(4) compound 34 is subjected to deprotecting reaction of TBS protecting group-under acidic conditions and then undergoes acylation reaction with different anhydride (($R_{12}$)$_2$ CO) or acyl chloride ($R_{12}COCl$) to give compounds Ia and Ib with different substituents.

Specifically, the reaction in which compounds Ia and Ib are obtained from compound 34 is represented by the following general formula (II):

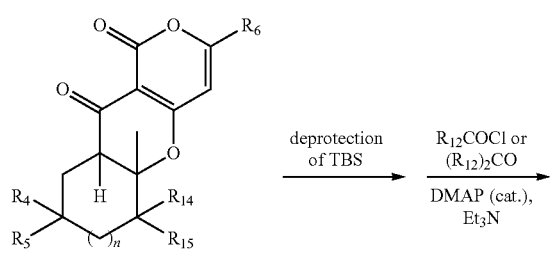

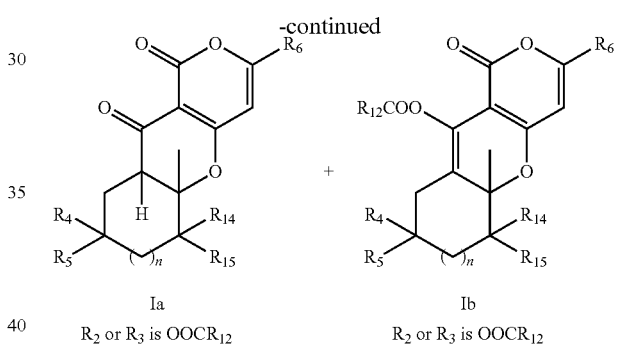

Ia
$R_2$ or $R_3$ is $OOCR_{12}$

Ib
$R_2$ or $R_3$ is $OOCR_{12}$

Further, (5) compound Ia undergoes Luche reduction reaction to give compound Ic;

or (6) compound Ia undergoes Corey-Bakshi-Shibata (CBS) asymmetric reduction reaction to give compound Ie containing an absolute configuration;

or (7) compound Ic is reacted with an acyl chloride including a different group ($R_{13}COCl$) to produce the compound Id of the present invention.

Wherein the definitions of $R_2$, $R_3$, $R_4$, $R_5$, $R_6$, n and W are the same as defined above; $R_{12}$, is substituted or unsubstituted 5- to 8-membered aryl or heteroaryl group, C1 to C6 alkyl group, 3- to 8-membered cycloalkyl group; $R_{13}$ is substituted or unsubstituted 5- to 8-membered aryl or heteroaryl group, C1 to C6 alkyl group, 3- to 8-membered cycloalkyl group; wherein the term of "substituted" means to be substituted with halogen, hydroxy, alkyl, alkoxy, amino, cyano; one of $R_{14}$ and $R_{15}$ is hydrogen and the other is tert-butyldimethylsilyloxy group.

Wherein the solvent used in the coupling reaction in step (1) is selected from aprotic solvents such as tetrahydrofuran; the reaction temperature is −30° C. to room temperature;

the solvent used in the solvolysis reaction in step (2) is selected from the group consisting of toluene and methanol; the reaction temperature is 80° C.;

the solvent used in the C-acylation ring-closing reaction in step (3) is selected from aprotic solvents such as tetrahydrofuran; the reaction temperature is from 0° C. to room temperature;

the solvent used in the deprotecting reaction of TBS protecting group—and the acylation reaction in step (4) is selected from aprotic solvents such as dichloromethane; the reaction temperature is room temperature;

the solvent used in the Luche reduction reaction in step (5) is selected from alcohol solvents, such as methanol and ethanol; the reaction temperature is −78° C.;

the solvent used in the Corey-Bakshi-Shibata (CBS) asymmetric reduction reaction in step (6) is selected from aprotic solvents such as tetrahydrofuran etc.; the reaction temperature is −78° C. or −30° C., the analogue of Pyripyropene A, represented by general formula (I), of the present invention can be used for preparing a medicine as an inhibitor having high selectivity toward ACAT2, and thus can be used for preparing a medicine for the treatment of atherosclerosis.

DETAILED EMBODIMENTS

The present invention will be further described below with reference to specific examples, but the present invention is not limited to these examples.

Preparation Examples of the Compounds

In the following Preparation Examples, NMR was measured using a Mercury-Vx 300M instrument manufactured by Varian, NMR calibration: δ H 7.26 ppm (CDCl$_3$), 2.50 ppm (DMSO-d$_6$), 3.15 ppm (CD$_3$OD); the reagents were mainly provided by Shanghai Chemical reagent Co., Ltd; the silica gel plate (Model No.: HSGF 254) used in TLC thin layer chromatography was produced by HuiyouSilica Gel Development Co., Ltd, Yantai, Shandong; silica gel used in the normal phase column chromatography for compound purification was produced by the branch of Ocean chemical Plant in Qingdao, Shandong, Model No.: zcx-11, 200-300 mesh.

Preparation Example 1 (Compound Nos.: 2 and 6)

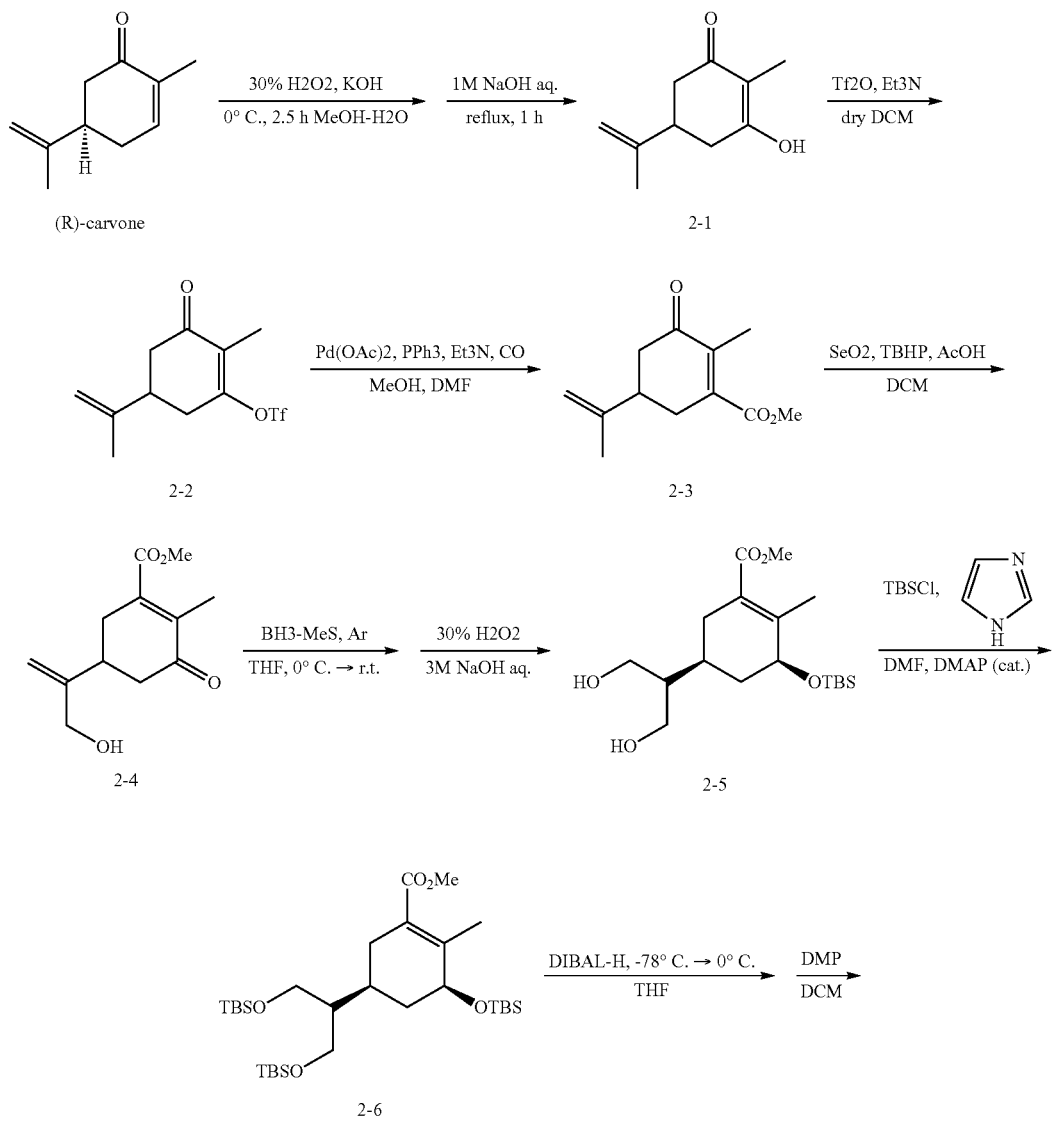

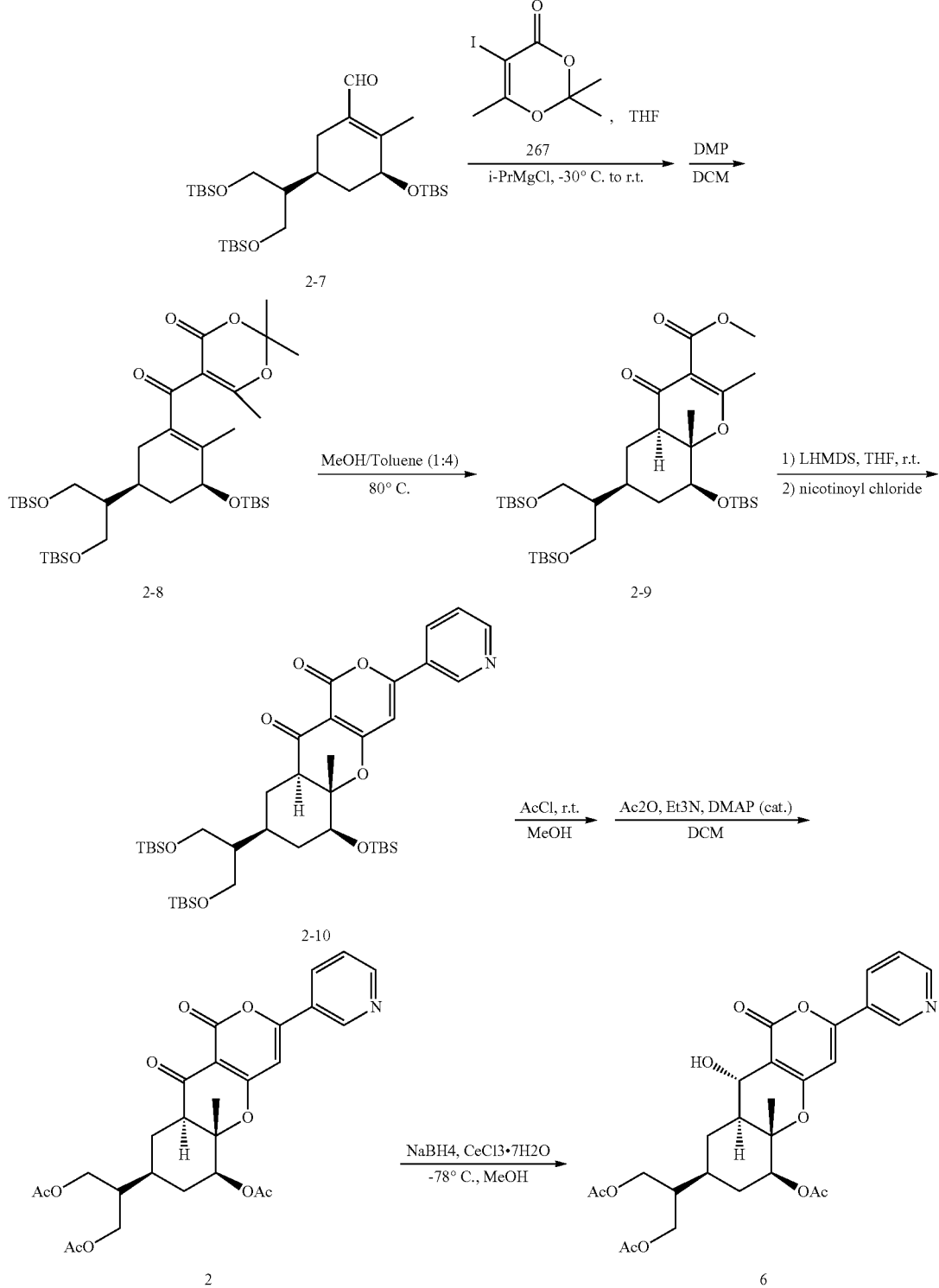

40 ml of a methanol solution containing 40.0 g (0.266 mol) of (R)-carvone was cooled to 0° C., and then a mixed solution of 40 ml of water and 120 ml of methanol containing 32.0 g (0.57 mol) of KOH was added. The resulting mixture was cooled to −5° C., and then 30 ml of 30% H₂O₂ was added. After 10 minutes, the temperature was elevated to 15° C. The mixture was stirred for 25 minutes and then cooled to −3° C. Another 35 ml of 30% H₂O₂ was added to the mixture, and the resulting mixture was stirred for 2.5 hours at 0° C. After the reaction was complete which was monitored by TLC, the reaction was quenched with a lot of crushed ice. Then the resultant was extracted with ethyl acetate, washed with brine, dried and concentrated. After adding 1 L 1 mol/l aqueous sodium hydroxide solution to the crude product in an ice bath, the resultant was heated under reflux for 1 hour, then cooled to room temperature, and 20% hydrochloric acid was added thereto under low temperature to adjust the pH to be acidic, followed by filtration, to give a light yellow solid as product 2-1 (total 29.8 g, 67%): $^1$H NMR (CDCl$_3$, 300 MHz) δ 4.83 (dd, J=13.8, 15.3 Hz, 2H), 2.74-2.41 (m, 5H), 1.74 (s, 3H), 1.69 (s, 3H).

Triethylamine (302 mg, 2.98 mmol) was added to a solution of compound 2-1 (380 mg, 2.29 mmol) in dichloromethane at 0° C. After stirring for 5 min, trifluoromethanesulfonic anhydride (0.50 ml, 2.98 mmol) was added. The resultant was stirred for 1 hour at 0° C., after the reaction was complete which was monitored by TLC, the resultant was purified using flash column chromatography which was eluted with petroleum ether/ether (v/v)=1/1 to give the product 2-2 (726 mg, 2.44 mmol, quantitative): $^1$H NMR (CDCl$_3$, 300 MHz) δ4.87 (s, 1H), 4.79 (s, 1H), 2.79-2.36 (m, 5H), 1.84 (s, 3H), 1.75 (s, 3H);

Compound 2-2 was dissolved in MeOH (2.0 ml) and DMF (3.0 ml), and then Pd(OAc)$_2$ (8.0 mg, 0.04 mmol), PPh$_3$ (11.0 mg, 0.04 mmol) and Et$_3$N (0.15 ml, 1.02 mmol) were added, with a carbon monoxide balloon mounted, the mixture was refluxed overnight. The resultant was cooled to room temperature next day, diluted with ethyl acetate, washed with water and brine, dried and concentrated, isolated and purified by column chromatography (n-hexane/ethyl acetate (v/v)=25:1) to give the product methyl ester 2-3 as clear oil (50 mg, 0.24 mmol, 71%): $^1$H NMR (CDCl$_3$, 300 MHz) δ4.81 (s, 1H), 4.75 (s, 1H), 3.80 (s, 3H), 2.72-2.30 (m, 5H), 1.92 (s, 3H), 1.79 (s, 3H).

Selenium dioxide (50 mg, 0.241 mmol) was dissolved in dichloromethane, tert-butyl hydroperoxide (0.09 ml, 0.482 mmol) was added dropwise thereto, then the mixture was cooled to 0° C., acetic acid (0.002 ml, 0.0241 mmol) was added. After about 30 minutes, the selenium dioxide was completely dissolved, followed by addition of the solution of the compound 2-3 in dichloromethane. The mixture was elevated to room temperature and stirred for 36 hours. When the raw materials were almost exhausted, the resultant was diluted with ethyl acetate, washed with 10% potassium hydroxide aqueous solution, washed with brine, dried and concentrated. The resultant was isolated by column chromatography (dichloromethane:methanol (v/v)=50:1) to give compound 2-4 as a light yellow oil product (8 mg, 14.87%). $^1$H NMR (d-DMSO, 300 MHz) δ 5.18 (s, 1H), 4.97 (s, 1H), 4.15 (s, 2H), 3.82 (s, 3H), 2.83-2.37 (m, 5H), 1.87 (s, 3H).

BH$_3$-Me$_2$S (0.54 ml, 5.35 mmol) was added dropwise to a solution of compound 2-4 (400 mg, 1.78 mmol) in tetrahydrofuran at 0° C., then the mixture was warmed to room temperature, stirred for 2 h, then cooled to 0° C., 20 ml of a solution of THF and MeOH in a ratio of 1:1 was added thereto, followed by addition of an aqueous solution (17.7 ml) of 30% H$_2$O$_2$ (7.6 ml) and 3M NaOH. The mixture was warmed to room temperature and stirred for 2 h. After raw materials were exhausted, which was monitored by TLC, the resultant was diluted with ethyl acetate, washed with 10% Na$_2$SO$_3$ aqueous solution, and washed with brine, dried and concentrated, isolated by column chromatography (dichloromethane:methanol (v/v)=10:1) to give the product trihydroxy compound 2-5 (180 mg, 41.31%). $^1$H NMR (CD$_3$OD, 300 MHz) δ4.12 (br s, 1H), 3.72 (s, 3H), 3.74-3.62 (m, 4H), 2.42 (d, J=16.2 Hz, 1H), 2.18-2.09 (m, 2H), 1.99-1.83 (m, 1H), 1.59-1.22 (m, 1H), 1.32-1.24 (m, 1H).

Compound 2-5 (180 mg, 0.737 mmol) was dissolved in DMF, followed by adding imidazole (302 mg, 4.43 mmol), DMAP (cat.). After stirring for 5 min, TBSCl (667 mg, 4.43 mmol) was added and the mixture was stirred overnight at room temperature. The reaction was quenched with water, the reaction solution was extracted with ethyl acetate. The organic phase was washed with brine, dried and concentrated. The resultant was purified by column chromatography (n-hexane:ethyl acetate (v/v)=50:1) to give compound 2-6 (310 mg, yield 80%). $^1$H NMR (CDCl$_3$, 300 MHz) δ4.16 (brs, 1H), 3.71 (s, 3H), 3.68-3.56 (m, 4H), 2.34 (d, J=16.2 Hz, 1H), 2.13-2.03 (m, 2H), 2.01 (s, 3H), 1.87-1.76 (m, 1H), 1.63-1.41 (m, 1H), 1.34 (dd, J=8.7, 18.9 Hz, 1H), 0.88 (s, 27H), 0.03 (s, 18H).

DIBAL-H (1.2 ml, 1.17 mmol) was added dropwise to a solution of compound 2-6 (310 mg, 0.529 mmol) in THF in a dry ice/acetone bath. After completion of addition, the mixture was warmed to room temperature and stirred for 2 h. When the raw material was exhausted, which was monitored by TLC, the reaction was quenched with saturated NaHCO$_3$ aqueous solution, and the mixture was warmed to room temperature, filtered by suction, washed with ether, and the filtrate was washed with brine, dried over anhydrous sodium sulfate, concentrated, and directly used to the next step. The crude product was dissolved in dichloromethane and DMP (270 mg, 0.635 mmol) at 0° C., the mixture was warmed to room temperature and stirred for 1 h. The reaction was quenched with saturated sodium thiosulfate solution/saturated sodium bicarbonate solution (v/v)=1/1, and the resultant was extracted with dichloromethane, washed with brine, concentrated, and purified by column chromatography (n-hexane/ethyl acetate (v/v)=50/1) to give product 2-7 (185 mg, yield 63%). $^1$H NMR (CDCl$_3$, 300 MHz) δ10.14 (s, 1H), 4.27 (s, 1H), 3.76-3.58 (m, 4H), 2.45 (d, J=13.2 Hz, 1H), 2.15 (s, 3H), 1.89-1.08 (m, 5H), 0.92 (s, 27H), 0.03 (s, 18H).

Iodide 267 (311 mg, 1.16 mmol) was dissolved in dry THF and cooled to −30° C. Isopropylmagnesium chloride (0.6 ml, 1.16 mmol) was added and stirred for 30 minutes at this temperature, followed by addition of a solution of compound 2-7 (214 mg, 0.385 mmol) in THF. The mixture was warmed to room temperature and stirred for 30 minutes and then the reaction was quenched with saturated ammonium chloride solution. The resultant was extracted with ethyl acetate, the organic phase was washed with brine, dried over anhydrous sodium sulfate and concentrated, and directly subjected to the next step. The crude product was dissolved in dichloromethane and DMP (245 mg, 0.580 mmol) was added at 0° C., the mixture was stirred overnight at room temperature. The next day, the reaction was quenched with a mixture of saturated sodium thiosulfate solution and saturated sodium bicarbonate solution (saturated sodium thiosulfate solution/saturated sodium bicarbonate solution=1/1), the resultant was extracted with dichloromethane, washed with brine, concentrated, and purified by column chromatography (n-hexane/ethyl acetate (v/v)=25/1) to give product 2-8 (87 mg, yield 33%). $^1$H NMR (CDCl$_3$, 300 MHz) δ4.21 (brs, 1H), 3.72-3.56 (m, 4H), 2.24 (s, 3H), 2.14-1.86 (m, 4H), 1.52-1.46 (m, 1H), 1.41 (q, J=13.3 Hz, 1H), 0.94 (s, 27H), 0.03 (s, 6H), 0.02 (s, 12H).

Compound 2-8 (80 mg, 0.115 mmol) was dissolved in toluene (2 ml) and methanol (0.5 ml), and the reaction mixture was heated to an external temperature of 80° C. and refluxed overnight. The next day, the resultant was concentrated and isolated by column chromatography (n-hexane/ethyl acetate (v/v)=10/1) to give product 2-9 (77 mg, yield 99%). $^1$H NMR (CDCl$_3$, 300 MHz) δ3.82 (dd, J=4.8, 11.1 Hz, 1H), 3.79 (s, 3H), 3.67-3.55 (m, 4H), 2.46 (dd, J=12.3, 3.6 Hz, 1H), 2.25 (s, 3H), 2.07 (d, J=14.2 Hz, 1H), 1.82 (d, J=13.8 Hz, 1H), 1.63-1.1.47 (m, 2H), 1.32 (dd, J=12.9, 24.6 Hz, 1H), 1.19 (s, 3H), 1.08 (dd, J=12.6, 26.1 Hz, 1H), 0.90 (s, 9H), 0.88 (s, 18H), 0.11 (s, 3H), 0.08 (s, 3H), 0.02 (s, 12H).

A solution of compound 2-9 (57 mg, 0.085 mmol) in THF was added dropwise to a solution of LHMDS (1 ml, 0.85 mmol) in THF at 0° C., the mixture was warmed to room temperature and stirred for 4 h. The nicotinoyl chloride hydrochloride was added quickly the resultant was stirred for 2 h at room temperature. When the raw materials were exhausted, which was monitored by TLC, the reaction was quenched with 2 ml of acetic acid, the resultant was diluted with 10 ml of water, extracted with dichloromethane, dried over anhydrous sodium sulfate and concentrated. The resultant was purified by column chromatography (n-hexane/acetone (v/v)=3/1) to give the product 2-10 as a yellow solid (30 mg, yield 47.4%). $^1$H NMR (CDCl$_3$, 300 MHz) δ9.04 (s, 1H), 8.73 (d, J=3.3 Hz, 1H), 8.17 (d, J=8.1 Hz, 1H), 7.44 (dd, J=4.8, 8.1 Hz, 1H), 6.48 (s, 1H), 3.93 (dd, J=4.8, 11.4 Hz, 1H), 3.69-3.58 (m, 4H), 2.61 (dd, J=3.6, 12.3 Hz, 1H), 2.19 (d, J=14.1 Hz, 1H), 1.87 (d, J=12.9 Hz, 1H), 1.68-1.63 (m, 1H), 1.54 (dd, J=5.7, 11.1 Hz, 1H), 1.39 (dd, J=12.9, 24.6 Hz, 1H), 1.29 (s, 3H), 1.27-1.18 (m, 1H), 0.87 (s, 27H), 0.18 (s, 6H), 0.13 (s, 6H).

Acetyl chloride (13 μl, 0.175 mmol) was added dropwise to 0.1 ml of methanol, and the mixture was stirred for 5 minutes at room temperature. Subsequently, a solution of the compound 2-10 (13 mg, 0.018 mmol) in methanol was added and the mixture was stirred for 1 hour at room temperature. The resultant was concentrated and directly subjected to the next step. The crude product was dissolved in dichloromethane, and a catalytic amount of DMAP, triethylamine (25 μl, 0.175 mmol), acetic anhydride (9 μl, 0.09 mmol) were added and the mixture was stirred for half an hour at room temperature. After the reaction is complete, which was monitored by TLC, the reaction was quenched with water. The resultant was extracted with ethyl acetate, dried over anhydrous sodium sulfate, concentrated and directly subjected to the next step.

Crude product 2 (10 mg, 0.019 mmol) and cerium(III) chlorideheptahydrate (50 mg, 0.133 mmol) were dissolved in methanol and cooled to −78° C. Sodium borohydride (5.1 mg, 0.133 mmol) was carefully added and the mixture was stirred for 30 minutes and the raw materials disappeared. The reaction was quenched with acetone, and the resultant was diluted with ethyl acetate. The organic phase was washed with water, washed with brine, dried, concentrated and purified by column chromatography (dichloromethane/methanol (v/v)=25/1) to give the final product 6 as a light yellow solid (9 mg, 90%): $^1$H NMR (CDCl$_3$, 300 MHz) δ9.25 (s, 1H), 8.87 (s, 1H), 8.63 (s, 1H), 7.92 (s, 1H), 6.84 (s, 1H), 5.08-5.04 (m, 1H), 4.45 (d, J=10.2 Hz, 1H), 4.17-4.06 (m, 4H), 2.47-1.30 (m, 7H), 2.09 (s, 3H), 2.07 (s, 3H), 2.02 (s, 3H), 1.24 (s, 3H).

Preparation Example 2 (Compound No.: 7)

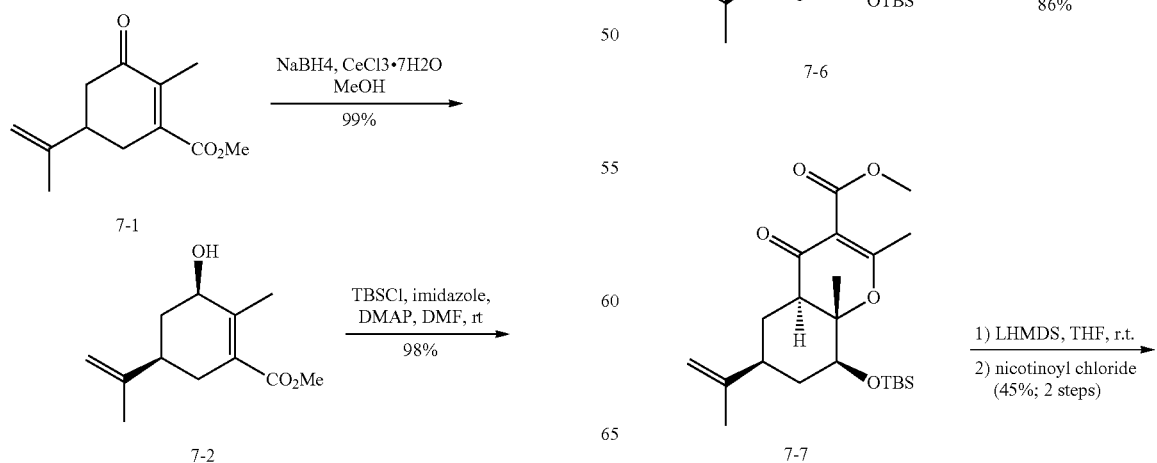

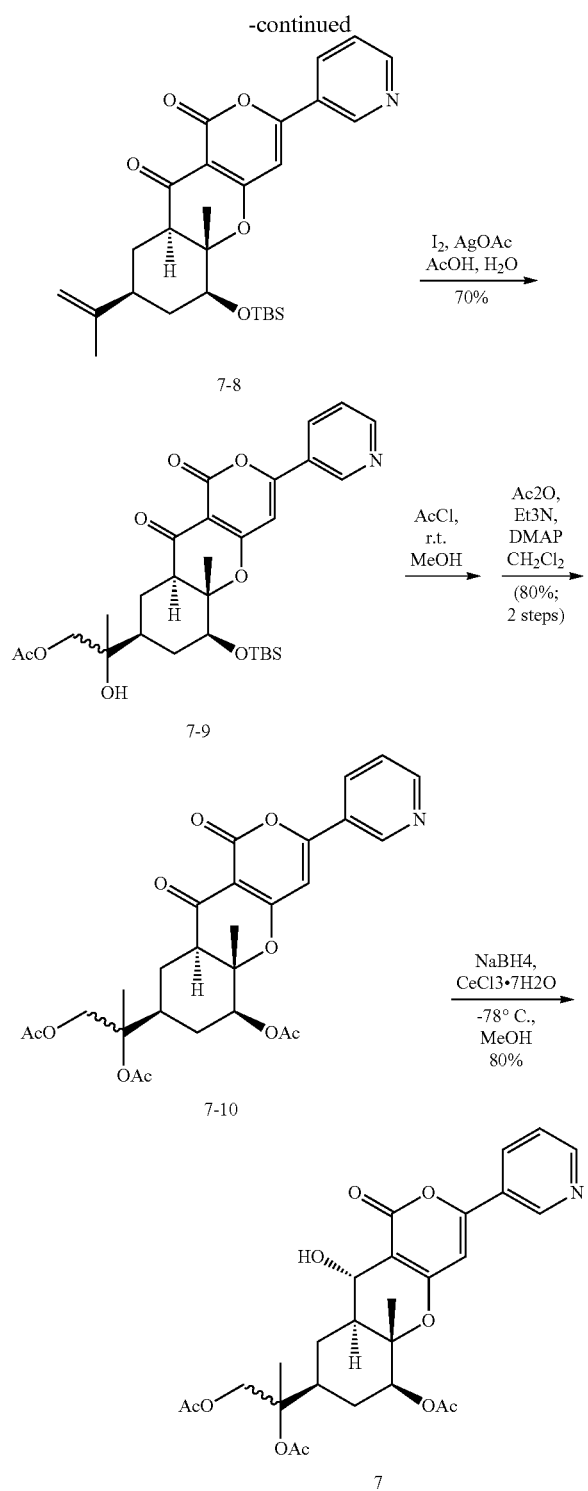

Compound 7-1 (3.298 g, 15.84 mmol) obtained from Preparation Example 1 as starting material and cerium(III) chloridehepthydrate (8.86 g, 23.76 mmol) were dissolved in methanol and cooled to 0° C. Sodium borohydride (899 mg, 23.76 mmol) was carefully added and the mixture was stirred for 30 minutes and the raw materials disappeared. The reaction was quenched with acetone, and the resultant was diluted with ethyl acetate. The organic phase was washed with water and brine, dried, concentrated and purified by column chromatography (petroleum ether/ethyl acetate (v/v)=10/1) to give the product 7-2 as clear oil (3.28 g, 99%): NMR (CDCl$_3$, 300 MHz) δ4.75 (dd, J=1.2, 5.7 Hz, 2H), 3.75 (brs, 1H), 3.71 (s, 3H), 2.45 (brd, J=14.4 Hz, 1H), 2.30-2.11 (m, 3H), 2.03 (s, 3H), 1.68 (s, 3H), 1.52 (td, J=12, 9.9 Hz, 1H). Compound 12 (2.35 g, 11.17 mmol) was dissolved in DMF, imidazole (1.60 g, 22.34 mmol) and DMAP (cat.) were added. After stirring for 5 min, TBSCl (3.40 g, 22.34 mmol) was added and the mixture was stirred overnight at room temperature. The next day, the reaction was quenched by addition of water, and the resultant was extracted with ethyl acetate. The organic phase was washed with brine, dried and concentrated. The resultant was isolated and purified by column chromatography (petroleum ether:ethyl acetate (v/v)=50:1) to give compound 7-3 as clear oil. (3.55 g, yield 98%). $^1$H NMR (CDCl$_3$, 300 MHz) δ4.74 (s, 2H), 4.24 (brs, 1H), 3.72 (s, 3H), 2.41 (brd, J=14.1 Hz, 1H), 2.23-2.02 (m, 3H), 1.98 (s, 3H), 1.68 (s, 3H), 1.52 (td, J=12.3, 10.2 Hz, 1H), 0.90 (s, 9H), 0.10 (s, 3H), 0.09 (s, 3H).

DIBAL-H (24.10 ml, 24.10 mmol) was added dropwise to a solution of compound 7-3 (3.55 g, 10.94 mmol) in THF in a dry ice/acetone bath. After completion of addition, the mixture was stirred for 2 h at room temperature. When the raw materials were exhausted which was monitored by TLC, the reaction was quenched by addition of saturated NaHCO$_3$ aqueous solution. The mixture was warmed to room temperature, subjected to filtration, washed with ether, then the filtrate was washed with brine, dried over anhydrous sodium sulfate, concentrated and directly subjected to the next step. The crude product was dissolved in dichloromethane, then DMP (5.60 g, 13.20 mmol) was added at 0° C., then the mixture was warmed to room temperature and stirred for 1 h. The reaction was quenched with saturated sodium thiosulfate solution/saturated sodium bicarbonate solution ((v/v)=1/1), and the resultant was extracted with dichloromethane, washed with brine, concentrated, and purified by column chromatography (n-hexane/ethyl acetate (v/v)=50/1) to give product 7-4 (2.928 g, yield 91%). $^1$H NMR (CDCl$_3$, 300 MHz) δ10.18 (s, 1H), 4.75 (s, 2H), 4.34 (brs, 1H), 2.52 (brd, J=15.3 Hz), 2.16 (s, 3H), 2.12-1.83 (m, 3H), 1.75 (s, 3H), 1.52 (td, J=12.6, 10.2 Hz, 1H), 0.93 (s, 9H), 0.14 (s, 3H), 0.12 (s, 3H).

Iodide 267 (656 mg, 2.45 mmol) was dissolved in dry THF and cooled to −30° C. A solution of 2 M isopropylmagnesium chloride in THF (1.5 ml, 2.45 mmol) was added dropwise, and the mixture was stirred for 30 minutes at this temperature. Then a solution of compound 7-4 (240 mg, 0.82 mmol) in THF was added, and the mixture was warmed to room temperature and stirred for 30 minutes. Subsequently, the reaction was quenched with a saturated ammonium chloride solution, and the resultant was extracted with ethyl acetate. The organic phase was washed with brine, dried over anhydrous sodium sulfate, concentrated, and directly subjected to the next step. The crude product 7-5 was dissolved in dichloromethane and DMP (519 mg, 1.23 mmol) was added at 0° C. and the mixture was warmed to room temperature and stirred overnight. The next day, saturated sodium thiosulfate solution/saturated sodium bicarbonate solution (v/v)=1/1 was added to quench the reaction, the resultant was extracted with dichloromethane, washed with brine, concentrated, and purified by column chromatography (n-hexane/ethyl acetate (v/v)=25/1) to give product 7-6 (157 mg, yield 45% in the two steps). $^1$H NMR (CDCl$_3$, 300 MHz) δ4.73 (s, 2H), 4.29 (s, 1H), 2.36 (dt, J=7.8, 1.8 Hz, 1H), 2.30 (s, 3H), 2.26-1.97 (m, 3H), 1.72 (s, 6H), 1.68 (s, 6H), 1.58 (td, J=12.6, 10.2 Hz, 1H), 0.88 (s, 9H), 0.08 (s, 6H).

Compound 7-6 (1.50 g, 3.46 mmol) was dissolved in toluene (60.0 ml) and methanol (15.0 ml). The reaction mixture was heated to an external temperature of 80° C. and refluxed overnight. The next day, the resultant was concentrated and isolated by column chromatography (n-hexane/ethyl acetate (v/v)=10/1) to give product 7-7 (yellow oil, 1.21 g, yield 86%). ¹H NMR (CDCl₃, 300 MHz) δ4.71 (s, 2H), 3.88 (dd, J=6.0, 12.0 Hz, 1H), 3.75 (s, 3H), 2.52 (dd, J=3.0, 12.0 Hz, 1H), 2.20 (s, 3H), 2.15-1.99 (m, 3H), 1.80-1.74 (m, 1H), 1.69 (s, 3H), 1.36 (td, J=12.6, 10.2 Hz, 1H), 1.19 (s, 3H), 0.88 (s, 9H), 0.09 (s, 3H), 0.07 (s, 3H).

A solution of compound 7-7 (78.00 mg, 0.19 mmol) in THF was added dropwise to a solution of 1 M LHMDS (2.00 ml, 2.00 mmol) in THF at 0° C. and the mixture was stirred for 4 h at room temperature. Nicotinoyl chloride hydrochloride was added quickly, and stirred for 2 h at room temperature. When the raw materials were exhausted which was monitored by TLC, the reaction was quenched by addition of acetic acid, and the resultant was diluted with water, extracted with dichloromethane, dried over anhydrous sodium sulfate and concentrated. The resultant was purified by column chromatography (n-hexane/acetone (v/v)=3/1) to give an important intermediate 7-8 as a white solid (41.00 mg, yield 45% in two steps), ¹H NMR (CDCl₃, 300 MHz) δ9.06 (d, J=1.2 Hz, 1H), 8.75 (d, J=3.6 Hz, 1H), 8.19 (d, J=8.4 Hz, 1H), 7.45 (dd, J=4.8, 8.1 Hz, 1H), 6.50 (s, 1H), 4.89 (s, 2H), 4.03 (dd, J=10.8, 4.8 Hz, 1H), 2.71 (d, J=12.3, 3.6 Hz, 1H), 2.28 (d, J=13.5 Hz, 1H), 2.13 (t, J=12.9 Hz, 1H), 1.88 (d, J=13.8 Hz, 1H), 1.76 (s, 3H), 1.44 (q, J=12.9 Hz, 1H), 1.34 (s, 3H), 1.31-1.23 (m, 1H), 0.96 (s, 9H), 0.07 (s, 3H), 0.04 (s, 3H).

Compound 7-8 (134 mg, 0.279 mmol) was dissolved in glacial acetic acid (7.4 ml) and water (0.03 ml). Silver acetate (100 mg, 0.594 mmol) and iodine (83 mg, 0.327 mmol) were added and the mixture was stirred overnight at room temperature. The next day, the resultant was added with water and extracted with ethyl acetate. The organic phase was washed with brine, concentrated by rotary evaporation, isolated by column chromatography (dichloromethane/methanol (v/v)=25/1) to give compound 7-9, which contained a pair of diastereomers 7-9-a (33 mg) and 7-9-b (44 mg). 7-9-a: ¹H NMR (CDCl₃, 400 MHz) δ9.03 (d, J=2.8 Hz, 1H), 8.73 (d, J=4.8 Hz, 1H), 8.16 (dd, J=2.8, 10.4 Hz, 1H), 7.44 (dd, J=6.8, 11.2 Hz, 1H), 6.44 (s, 1H), 4.08 (dd, J=12.0, 32.0 Hz, 2H), 4.00 (dd, J=4.0, 8.0 Hz, 1H), 2.68 (dd, J=4.0, 16.0 Hz, 1H), 2.21 (d, J=16.0 Hz, 1H), 2.11 (s, 3H), 2.01 (d, J=12.0 Hz, 1H), 1.72 (t, J=12.0 Hz, 1H), 1.37 (dd, J=12.0, 24.0 Hz, 1H), 1.31 (s, 3H), 1.20 (s, 3H), 1.15 (dd, J=8.0, 24.0 Hz, 1H), 0.95 (s, 9H), 0.19 (s, 3H), 0.14 (s, 3H).

7-9-b: ¹H NMR (CDCl₃, 400 MHz) δ9.05 (s, 1H), 8.75 (d, J=4.0 Hz, 1H), 8.18 (d, J=8.0 Hz, 1H), 7.45 (dd, J=4.0, 8.0 Hz, 1H), 6.43 (s, 1H), 4.07 (dd, J=12.0, 32.0 Hz, 2H), 3.98 (dd, J=4.0, 8.0 Hz, 1H), 2.66 (dd, J=4.0, 16.0 Hz, 1H), 2.36 (d, J=16.0 Hz, 1H), 2.12 (s, 3H), 1.89 (d, J=12.0 Hz, 1H), 1.70 (t, J=12.0 Hz, 1H), 1.37-1.26 (m, 2H), 1.32 (s, 3H), 1.22 (s, 3H), 0.95 (s, 9H), 0.19 (s, 3H), 0.14 (s, 3H).

Acetyl chloride (0.06 ml, 0.6 mmol) was added dropwise to 0.7 ml of methanol, and the mixture was stirred for 5 minutes at room temperature. Subsequently, a solution of compound 7-9 (33 mg, 0.060 mmol) in methanol was added and the mixture was stirred for 1 hour at room temperature. After concentrated, the resultant was directly subjected to the next step. The crude product was dissolved in dichloromethane and a catalytic amount of DMAP, triethylamine (0.09 ml, 0.60 mmol), acetic anhydride (0.04 ml, 0.30 mmol) was added and the mixture was stirred overnight at room temperature. After the reaction was complete which was monitored by TLC, the reaction was quenched by addition of water, and the resultant was extracted with ethyl acetate, dried over anhydrous sodium sulfate, concentrated, isolated and purified by column chromatography (dichloromethane/methanol (v/v)=50/1) to give the compound 7-10 as a yellow solid (yield 80%). Since compounds 7-9-a and 7-9-b were isolated from 7-9 in the last step, the corresponding compounds 7-10-a and 7-10-b were obtained.

7-10-a: ¹H NMR (CDCl₃, 400 MHz) δ9.11 (s, 1H), 8.79 (s, 1H), 8.22 (d, J=8.0 Hz, 1H), 7.48 (s, 1H), 6.55 (s, 1H), 5.33 (dd, J=4.0, 8.0 Hz, 1H), 4.47 (dd, J=12.0, 100.0 Hz, 2H), 2.82 (dd, J=4.0, 8.0 Hz, 1H), 2.23-1.86 (m, 3H), 2.22 (s, 3H), 2.11 (s, 3H), 2.05 (s, 3H), 1.59-1.29 (m, 2H), 1.52 (s, 3H), 1.45 (s, 3H).

7-10-b: ¹H NMR (CDCl₃, 400 MHz) δ9.08 (s, 1H), 8.76 (d, J=4.0 Hz, 1H), 8.19 (d, J=4.0 Hz, 1H), 7.46 (dd, J=4.0, 8.0 Hz, 1H), 6.55 (s, 1H), 5.29 (dd, J=4.0, 8.0 Hz, 1H), 4.44 (dd, J=8.0, 48.0 Hz, 2H), 2.79 (dd, J=4.0, 8.0 Hz, 1H), 2.38-1.97 (m, 3H), 2.19 (s, 3H), 2.10 (s, 3H), 2.03 (s, 3H), 1.57-1.28 (m, 2H), 1.47 (s, 3H), 1.43 (s, 3H).

Compound 7-10 (11 mg, 0.021 mmol) and cerium(III) chlorideheptahydrate (55 mg, 0.147 mmol) were dissolved in methanol and cooled to −78° C. Then sodium borohydride (5.6 mg, 0.147 mmol) was added carefully, and the mixture was stirred for 30 minutes and the raw materials disappeared. The reaction was quenched with acetone, and the resultant was diluted with ethyl acetate. The organic phase was washed with water, washed with brine, dried, concentrated, isolated and purified by column chromatography (dichloromethane/methanol=50/1) to give final product 7 as a light yellow solid (8.5 Mg, yield 78%): ¹HNMR (CDCl₃, 400 MHz) δ9.01 (d, J=4.0 Hz, 1H), 8.69 (dd, J=4.0, 8.0 Hz, 1H), 8.09 (td, J=4.0, 8.0 Hz, 1H), 7.41 (dd, J=4.0, 8.0 Hz, 1H), 6.49 (s, 1H), 5.08 (dd, J=4.0, 8.0 Hz, 1H), 4.56-4.34 (m, 3H), 2.34-1.99 (m, 2H), 2.17 (s, 3H), 2.07 (s, 3H), 1.99 (s, 3H), 1.89 (t, J=12.0 Hz, 1H), 1.58-1.51 (m, 1H), 1.48 (s, 3H), 1.30 (s, 3H), 1.13 (dd, J=12.0, 24.0 Hz, 1H).

Preparation Example 3 (Compound Nos.: 1, 4 and 5)

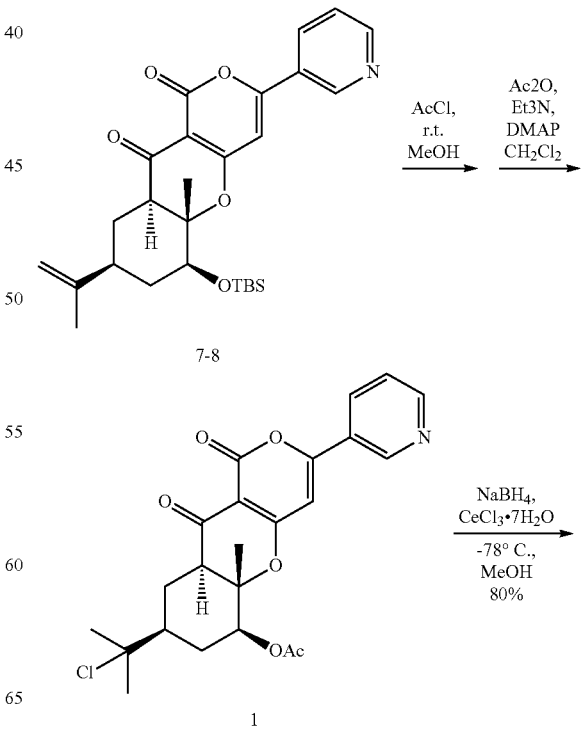

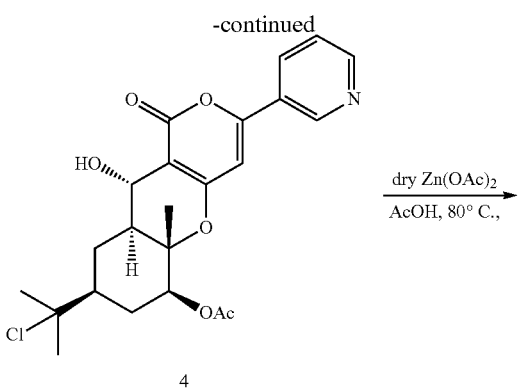

4

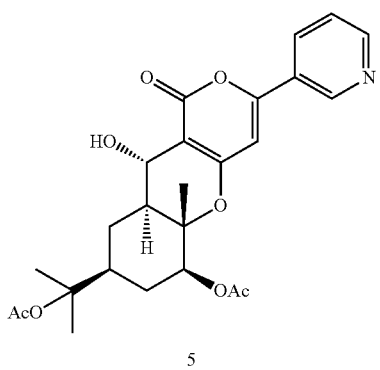

5

Compound 7-8 (28 mg, 0.059 mmol) obtained from Preparation Example 2 as starting material was dissolved in MeOH, and acetyl chloride (44 μl, 0.58 mmol) was added dropwise thereto. The mixture was stirred for 1 hour at room temperature. After concentrated, the mixture was directly subjected to the next step. The crude product was dissolved in dichloromethane and a catalytic amount of DMAP, triethylamine (85 μl, 0.59 mmol), acetic anhydride (30 μl, 0.295 mmol) were added and the mixture was stirred for 30 minutes at room temperature. After the reaction was complete which was monitored by TLC, the reaction was quenched by addition of water, and the resultant was extracted with ethyl acetate. The organic phase was dried over anhydrous sodium sulfate, concentrated, isolated and purified by column chromatography (dichloromethane/methanol (v/v)=50/1) to give the compound 1 as a yellow solid (yield 80%): $^1$HNMR (CDCl$_3$, 300 MHz) δ9.06 (s, 1H), 8.74 (s, 1H), 8.17 (d, J=8.1 Hz, 1H), 7.44 (s, 1H), 6.54 (s, 1H), 5.29 (dd, J=5.4, 6.6 Hz, 1H), 2.99 (t, J=3.9 Hz, 1H), 2.83-2.74 (m, 1H), 2.46 (d, J=12.6 Hz, 1H), 2.30-1.98 (m, 2H), 1.80-1.69 (m, 1H), 2.17 (s, 3H), 1.63 (s, 3H), 1.60 (s, 3H), 1.32 (s, 3H).

Compound 4 (a yellow solid, yield 80%) was obtained in the same manner as the preparation method of compound 7 in Preparation Example 2: $^1$HNMR (CDCl$_3$, 300 MHz) δ8.99 (s, 1H), 8.68 (s, 1H), 8.09 (d, J=8.1 Hz, 1H), 7.40 (t, J=7.5 Hz, 1H), 6.49 (s, 1H), 5.06 (d, J=4.5 Hz, 1H), 4.47 (d, J=9.9 Hz, 1H), 2.47 (d, J=13.8 Hz, 1H), 2.40-1.72 (m, 5H), 2.22 (s, 3H), 1.68 (s, 3H), 1.66 (s, 3H), 1.24 (s, 3H).

Compound 4 (5.0 mg, 0.012 mmol) and anhydrous zinc acetate (5 mg, 0.024 mmol) were dissolved in glacial acetic acid and the mixture was heated to 80° C. overnight. The next day, the resultant was diluted with ethyl acetate, and the organic phase was washed with water and then washed with brine, dried and concentrated, isolated by thin layer chromatography (dichloromethane/methanol=25/1)) to give product 5 (a light yellow solid, yield 40%): $^1$HNMR (CDCl$_3$, 300 MHz) δ9.01 (s, 1H), 8.69 (s, 1H), 8.10 (d, J=8.1 Hz, 1H), 7.41 (s, 1H), 6.49 (s, 1H), 5.05 (d, J=4.8 Hz, 1H), 4.44 (d, J=5.1 Hz, 1H), 2.36 (d, J=10.2 Hz, 1H), 2.26 (s, 3H), 2.04 (s, 3H), 2.17-0.85 (m, 5H), 1.50 (s, 3H), 1.49 (s, 3H), 1.28 (s, 3H).

Preparation Example 4 (Compound Nos.: 13 and 14)

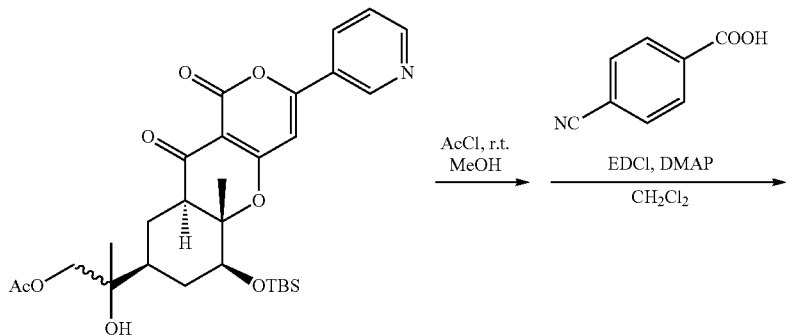

7-9

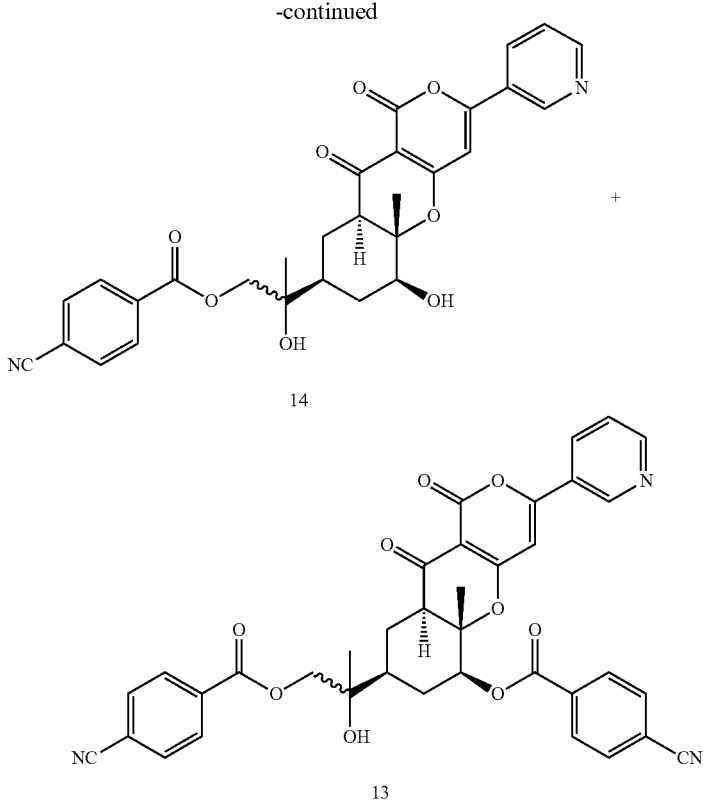

Acetyl chloride (0.07 ml, 0.951 mmol) was added dropwise to 0.4 ml of methanol, and the mixture was stirred for 5 minutes at room temperature. Subsequently, a solution of compound 7-9 (57 mg, 0.096 mmol) in methanol was added and the mixture was stirred for 1 hour at room temperature. The resultant was concentrated by rotary evaporation, and directly subjected to the next step. Crude product, p-cyanobenzoic acid, EDC.HCl and a catalytic amount of DMAP were dissolved in dichloromethane and the mixture was stirred overnight at room temperature. The next day, after the reaction was complete as shown by TLC, the reaction was quenched by addition of water. The resultant was extracted with ethyl acetate, dried over anhydrous sodium sulfate, concentrated, isolated and purified by column chromatography (dichloromethane/methanol (v/v)=50/1) to give compound 14 (5 mg, yield 10%): $^1$HNMR (CDCl$_3$, 300 MHz) δ8.94 (s, 1H), 8.58 (d, J=3.3 Hz, 1H), 8.12 (d, J=7.8 Hz, 2H), 8.06 (d, J=5.4 Hz, 1H), 7.66 (d, J=8.4 Hz, 2H), 7.40 (dd, J=4.8, 7.8 Hz, 1H), 6.73 (s, 1H), 4.24 (s, 2H), 3.95 (s, 1H), 3.54 (s, 1H), 2.64 (d, J=12.0 Hz, 1H), 1.97-1.40 (m, 4H), 1.39 (s, 3H), 1.27 (s, 3H), and 13 (16 mg, yield 32%): $^1$HNMR (CDCl$_3$, 300 MHz) δ9.01 (s, 1H), 8.73 (s, 1H), 8.26-8.11 (m, 5H), 7.83-7.77 (m, 4H), 7.43 (dd, J=8.1, 12.9 Hz, 1H), 6.48 (s, 1H), 5.72-5.68 (m, 1H), 4.52-4.26 (m, 2H), 2.90-2.83 (m, 1H), 2.40-1.09 (m, 5H), 1.64 (s, 3H), 1.31 (s, 3H).

The following compounds were synthesized in the same manner:

compound 11 was prepared by replacing the compound 7-9 in Preparation Example 4 with compound 7-8;

compound 12 was prepared by replacing the compound 7-10 in Preparation Example 2 with compound 11.

| Compound | Chemical structure | $^1$H NMR (CDCl$_3$, 300 MHz) data |
|---|---|---|
| 11 | 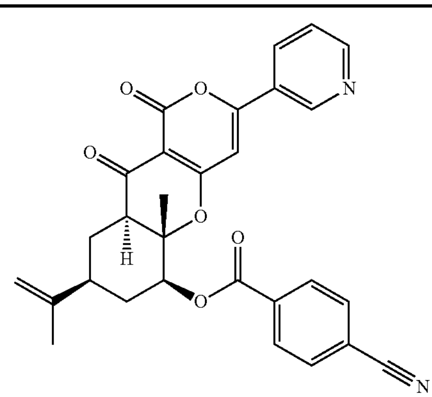 | δ 8.97 (s, 1H), 8.67 (d, J = 3.6 Hz, 1H), 8.18 (d, J = 9.0 Hz, 2H), 8.12-8.09 (m, 1H), 7.77 (d, J = 8.4 Hz, 2H), 7.38 (dd, J = 4.8, 7.8 Hz, 1H), 6.48 (s, 1H), 5.57 (dd, J = 4.8, 12.0 Hz, 1H), 4.78 (d, J = 4.5 Hz, 1H), 2.93-2.85 (m, 2H), 2.50-2.22 (m, 2H), 1.89-1.83 (m, 1H), 1.80 (s, 3H), 1.60 (s, 3H), 1.39 (dd, J = 12.6, 25.2 Hz, 1H). |

| Compound | Chemical structure | ¹H NMR (CDCl₃, 300 MHz) data |
|---|---|---|
| 12 | 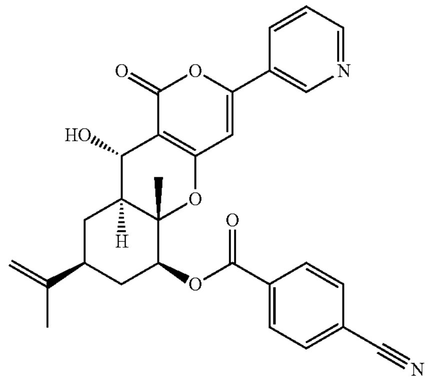 | δ 8.95 (s, 1H), 8.66 (d, J = 4.2, 1H), 8.19 (d, J = 4.2 Hz, 2H), 8.06 (d, J = 7.8 Hz, 1H), 7.79 (d, J = 7.8 Hz, 2H), 7.37 (dd, J = 4.2, 7.8 Hz, 1H), 6.42 (s, 1H), 5.38 (dd, J = 4.8, 11.7 Hz, 1H), 4.79 (d, J = 8.4 Hz, 2H), 4.52 (d, J = 10.2 Hz, 1H), 4.44 (s, 1H), 2.49-1.90 (m, 5H), 1.86 (s, 3H), 1.46 (s, 3H), 1.24 (dd, J = 12.6, 25.2 Hz, 1H). |
Preparation Example 5 (Compound Nos.: 8, 9 and 10)
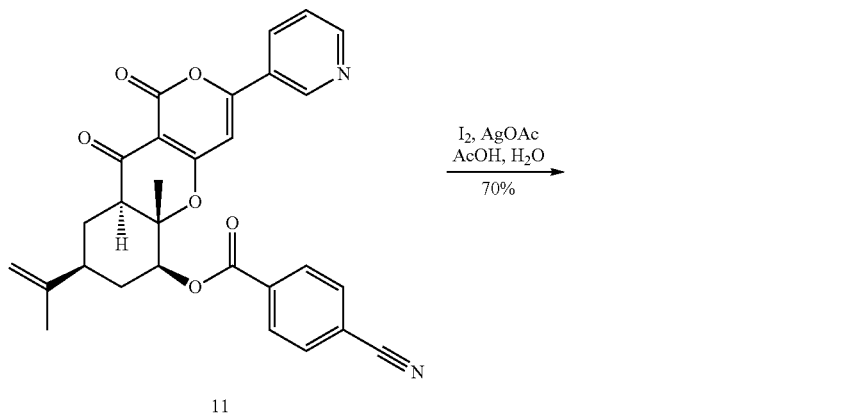
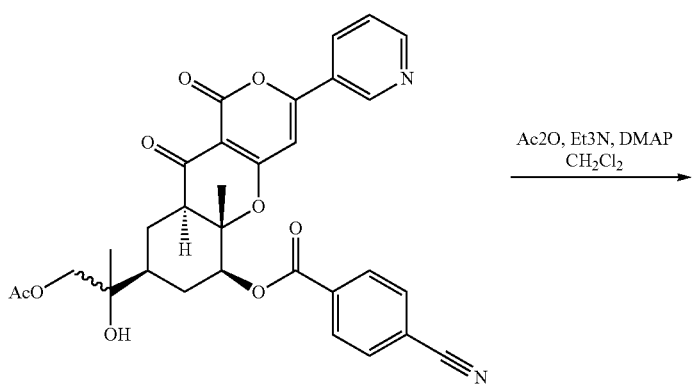

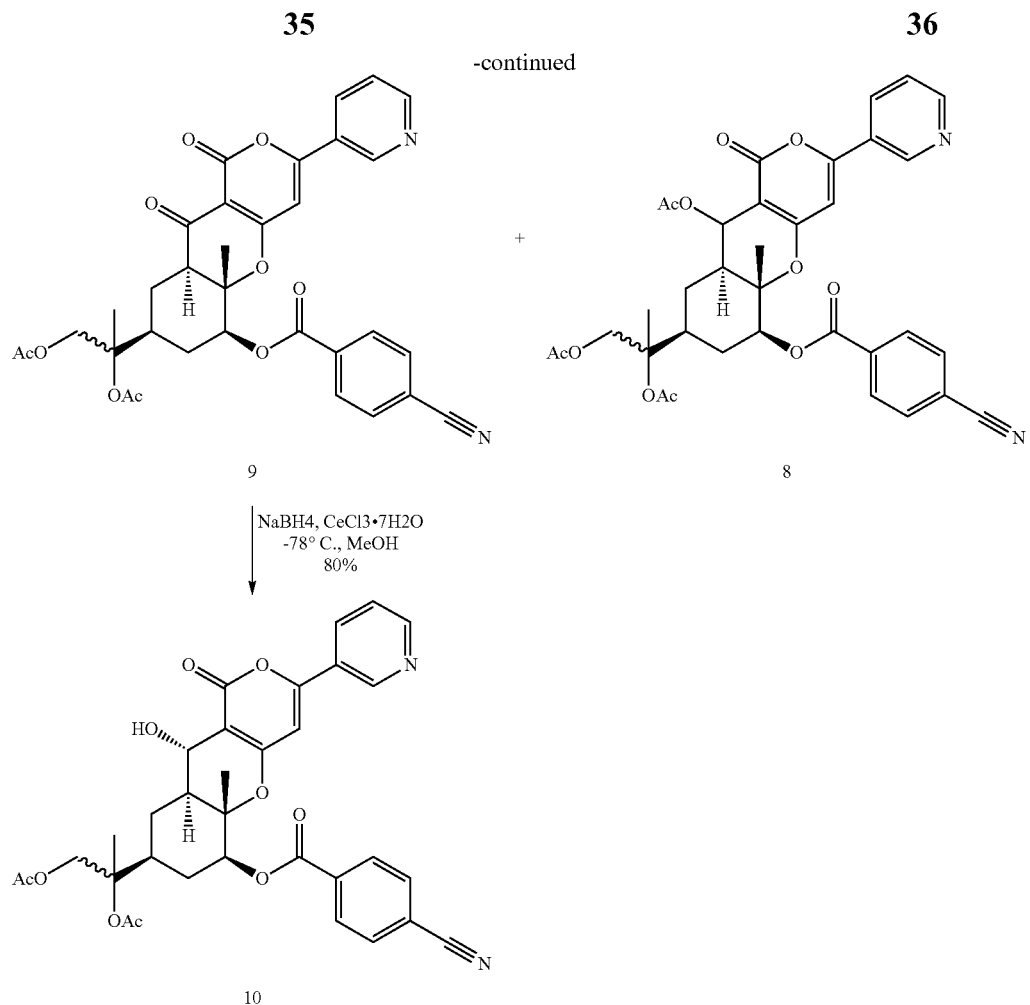

Compound 11 (30 mg, 0.061 mmol) obtained from example 5 was dissolved in glacial acetic acid (1.5 ml) and water (5.9 μl). Silver acetate (21 mg, 0.121 mmol) and iodine (17 mg, 0.665 mmol) were added, and the mixture was stirred overnight at room temperature. The next day, the resultant was added with water, and the mixture was extracted with ethyl acetate. The organic phase was washed with brine, concentrated by rotary evaporation, isolated by column chromatography (dichloromethane/methanol (v/v)=25/1) to give compound 9-1, which contained a pair of diastereomers, 16 mg in total (yield 46.3%). 9-1-a: $^1$H NMR (CDCl$_3$, 400 MHz) δ9.014 (s, 1H), 8.72 (d, J=4.8 Hz, 1H), 8.19 (d, J=8.1 Hz, 2H), 8.15 (d, J=7.8 Hz, 1H), 7.80 (d, J=8.7 Hz, 2H), 7.42 (dd, J=4.5, 8.1 Hz, 1H), 6.53 (s, 1H), 5.57 (dd, J=5.4, 12.3 Hz, 1H), 4.15 (s, 2H), 2.86 (d, J=9.0 Hz, 1H), 2.33 (d, J=4.5 Hz, 1H), 2.19 (s, 3H), 2.08-1.68 (m, 3H), 1.64 (s, 3H), 1.33 (dd, J=8.1, 21.6 Hz, 1H), 1.24 (s, 3H).

9-1-b: $^1$H NMR (CDCl$_3$, 400 MHz) δ9.014 (s, 1H), 8.72 (d, J=4.8 Hz, 1H), 8.19 (d, J=8.1 Hz, 2H), 8.15 (d, J=7.8 Hz, 1H), 7.80 (d, J=8.7 Hz, 2H), 7.42 (dd, J=4.5, 8.1 Hz, 1H), 6.53 (s, 1H), 5.57 (dd, J=5.4, 12.3 Hz, 1H), 4.15 (s, 2H), 2.86 (d, J=9.0 Hz, 1H), 2.45 (d, J=13.5 Hz, 1H), 2.19 (s, 3H), 2.08-1.68 (m, 3H), 1.64 (s, 3H), 1.39 (dd, J=12.9, 27.0 Hz, 1H), 1.24 (s, 3H).

Compound 9-1 (16 mg, 0.028 mmol) as starting material was dissolved in dichloromethane, and DMAP (cat.) was added thereto. Triethylamine (0.03 ml, 0.168 mmol) was added dropwise, and then acetic anhydride (0.02 ml, 0.084 Mmol) was added dropwise, and the mixture was stirred overnight at room temperature. The next day, the reaction was quenched with water, and the resultant was extracted with dichloromethane, concentrated and isolated by column chromatography (dichloromethane/methanol (v/v)=50/1) to give compound 9 (4.0 mg, yield 23.3%): $^1$HNMR (CDCl$_3$, 300 MHz) δ9.01 (s, 1H), 8.74 (s, 1H), 8.21-8.12 (m, 3H), 7.80 (t, J=8.4 Hz, 2H), 7.43 (dd, J=6.6, 13.8 Hz, 1H), 6.48 (s, 1H), 5.58-5.53 (m, 1H), 4.60-4.32 (m, 2H), 2.87 (d, J=9.3 Hz, 1H), 2.43-2.22 (m, 3H), 2.19 (s, 3H), 2.10 (s, 3H), 1.56-1.13 (m, 2H), 1.45 (s, 3H), 1.35 (s, 3H). and 8 (4.0 mg, yield 23.3%): $^1$HNMR (CDCl$_3$, 300 MHz) δ8.92 (d, J=2.1 Hz, 1H), 8.65 (d, J=4.8 Hz, 1H), 8.20 (dd, J=2.1, 8.4 Hz, 2H), 8.02 (d, J=8.1 Hz, 1H), 7.81 (d, J=8.4 Hz, 2H), 7.35 (dd, J=5.1, 8.4 Hz, 1H), 6.37 (s, 1H), 5.67 (s, 1H), 4.59-4.36 (m, 2H), 3.25-3.23 (m, 1H), 2.80-2.66 (m, 1H), 2.33 (s, 3H), 2.32-1.66 (m, 2H), 2.07 (s, 3H), 1.99 (s, 3H), 1.52 (s, 3H), 1.47 (s, 3H), 1.11-0.96 (m, 1H).

Compound 10 (yield 80%) was obtained in the same manner as the preparation method of compound 7 in Preparation Example 2: $^1$HNMR (CDCl$_3$, 300 MHz) δ9.01 (s, 1H), 8.64 (s, 1H), 8.21-8.12 (m, 3H), 7.80 (t, J=8.4 Hz, 2H), 7.43 (dd, J=6.6, 13.8 Hz, 1H), 6.43 (s, 1H), 5.38-5.27 (m, 1H), 4.58-4.32 (m, 3H), 2.62-1.57 (m, 5H), 2.19 (s, 3H), 2.10 (s, 3H), 1.45 (s, 3H), 1.35 (s, 3H), 0.92-0.85 (m, 1H).

Preparation Example 6 (Synthesis of the Chiral Compounds, Compound Nos.: 15-22)

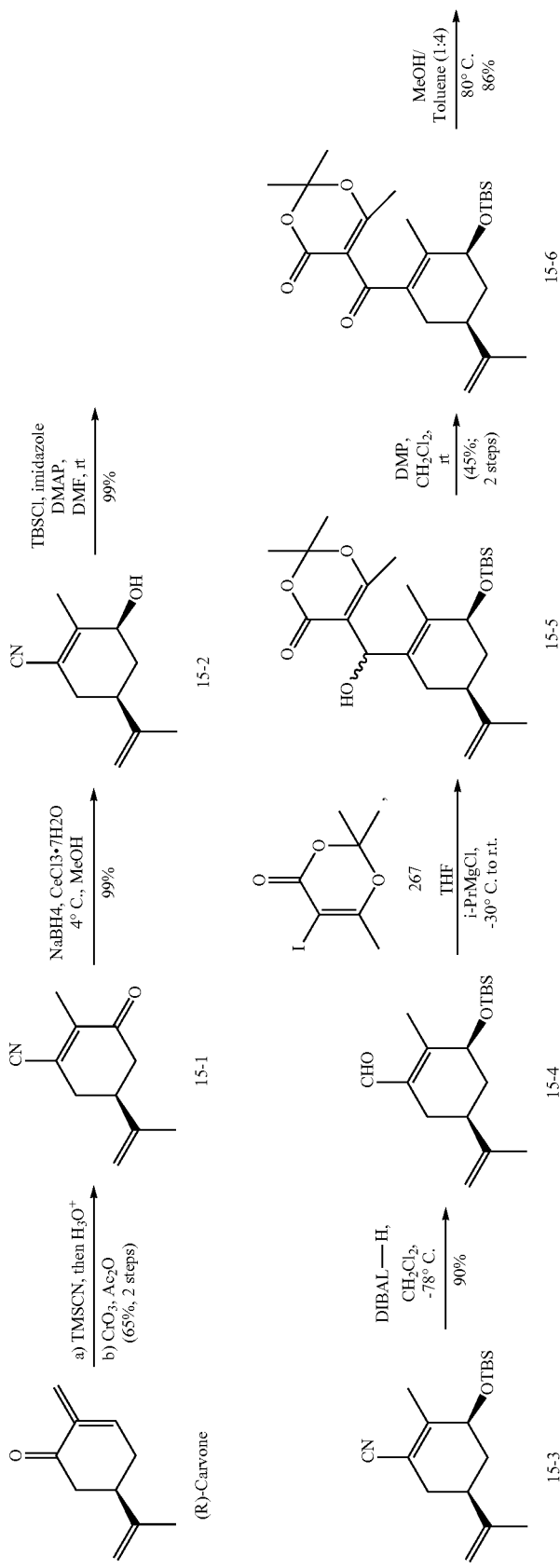

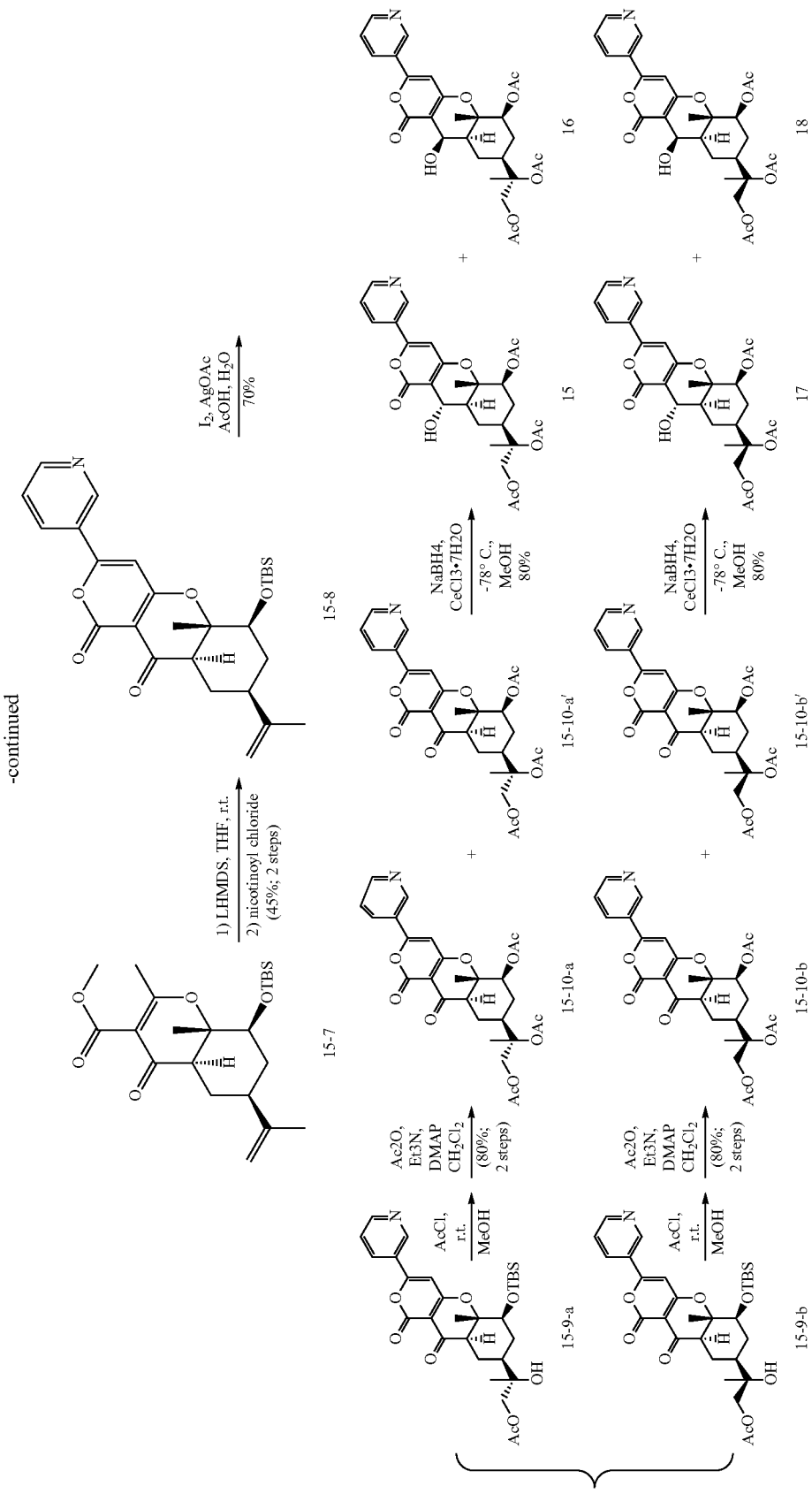

The raw material (R)-carvone (10.0 g, 66.6 mmol) readily obtained from natural sources as starting material and lithium salt of L-proline (810 mg, 6.66 mmol) were placed in a round bottom flask, and TMSCN (8.86 ml*2, 66.6 mmol*2) was slowly added thereto. The resulting suspension was stirred for 12 hours at room temperature and then 1 eq of TMSCN was added and the mixture was stirred for another 12 hours at room temperature. When the raw material was almost exhausted as shown by TLC, the mixture was diluted with 100 ml of THF and 100 ml of 1 M hydrochloric acid, and the mixture was stirred for 1 h at room temperature. Subsequently, the mixture was diluted with water, extracted with ether, and the organic phase was washed with brine, dried over anhydrous sodium sulfate and concentrated to give intermediate 177, which was directly subjected to the next step. Chromium trioxide (13.9 g, 139.2 mmol) was slowly added to acetic anhydride (54 ml) and the mixture was stirred at room temperature until completely dissolved. The resulting chromic acid reagent was then added dropwise to a solution of intermediate 177 in dichloromethane at −55° C., the resulting mixture was maintained at this temperature and stirred for half an hour. When the raw material was exhausted as shown by TLC, the reaction was quenched with methanol, and the resultant was diluted with water, extracted with dichloromethane. The organic phase was washed with saturated sodium bicarbonate aqueous solution and concentrated. The resultant was isolated by column chromatography (petroleum ether/ethyl acetate (v/v)=10/1) to give the product 15-1 as yellow oil (7.59 g, yield 65% in two steps): $^1$H NMR (CDCl$_3$, 300 MHz) δ4.87 (s, 1H), 4.77 (s, 1H), 2.78-2.32 (m, 5H), 2.06 (s, 3H), 1.68 (s, 3H).

Compound 15-1 (9.64 g, 55.02 mmol) and cerium(III) chlorideheptahydrate (20.5 g, 55.02 mmol) were dissolved in methanol and cooled in an ice-water bath. Sodium borohydride (2.1 g, 55.02 mmol) was added carefully, and the mixture was stirred for 30 minutes and the raw material disappeared. The reaction was quenched with acetone, the resultant was diluted with ethyl acetate, and the organic phase was washed with water, washed with brine, dried, concentrated, isolated and purified by column chromatography (petroleum ether/ethyl acetate (v/v)=10/1) to give product 15-2 as colorless, clear oil (11.14 mg, yield 99%): $^1$H NMR (CDCl$_3$, 300 MHz) δ4.77 (s, 1H), 4.72 (s, 1H), 4.19 (d, J=5.7 Hz, 1H), 2.73 (d, J=7.2 Hz, 1H), 2.30-2.08 (m, 4H), 2.06 (s, 3H), 1.71 (s, 3H), 1.49 (dd, J=12.6, 22.8 Hz, 1H). Compound 24 (11.14 g, 62.86 mmol) was dissolved in DMF and imidazole (8.60 g, 125.71 mmol) and DMAP (cat.) were added. After stirring for 5 min, TBSCl (18.95 g, 125.71 mmol) was added and the mixture was stirred overnight at room temperature. The next day, the reaction was quenched with water, and the resultant was extracted with ethyl acetate. The organic phase was washed with brine, dried and concentrated. The resultant was purified by column chromatography (petroleum ether:ethyl acetate (v/v)=25:1) to give compound 15-3 as colorless, clear oil (yield 98%): $^1$H NMR (CDCl$_3$, 300 MHz) δ4.75 (s, 1H), 4.71 (s, 1H), 4.24 (brs, 1H), 2.30-2.01 (m, 4H), 1.99 (s, 3H), 1.69 (s, 3H), 1.49 (dd, J=12.6, 22.8 Hz, 1H), 0.88 (s, 9H), 0.09 (s, 3H), 0.07 (s, 3H).

DIBAL-H (24.10 ml, 24.10 mmol) was added dropwise to a solution of compound 15-3 (3.55 g, 10.94 mmol) in THF in a dry ice/acetone bath and then the mixture was warmed to room temperature and stirred for 2 h. When the raw materials were exhausted which was monitored by TLC, the reaction was quenched by addition of saturated aqueous solution of potassium tartrate. The mixture was warmed to room temperature and stirred, extracted with dichloromethane, dried over anhydrous sodium sulfate, concentrated and isolated by column chromatography (petroleum ether/ethyl acetate (v/v)=25/1) to give the product 15-4 as yellow oil (14.75 g, yield 90%): $^1$H NMR (CDCl$_3$, 300 MHz) δ 10.15 (s, 1H), 4.71 (s, 2H), 4.34 (brs, 1H), 2.51 (d, J=14.4 Hz, 1H), 2.16 (s, 3H), 2.11 to 1.84 (m, 3H), 1.74 (s, 3H), 1.49 (dd, J=12.6, 22.8 Hz, 1H), 0.90 (s, 9H), 0.14 (s, 3H), 0.12 (s, 3H).

Iodide 267 (656 mg, 2.45 mmol) was dissolved in dry THF and cooled to −30° C. A solution of 2 M isopropylmagnesium chloride in THF (1.5 ml, 2.45 mmol) was added dropwise and the mixture was stirred for 30 minutes at this temperature. Then a solution of compound 15-4 (240 mg, 0.82 mmol) in THF was added and the mixture was warmed to room temperature and stirred for 30 minutes. And then the reaction was quenched with saturated ammonium chloride solution. After the resultant was extracted with ethyl acetate, the organic phase was washed with brine, dried over anhydrous sodium sulfate, concentrated and directly subjected to the next step. The crude product 15-5 was dissolved in dichloromethane and DMP (519 mg, 1.23 mmol) was added at 0° C., and the mixture was warmed to room temperature and stirred overnight. The next day, saturated sodium thiosulfate solution/saturated sodium bicarbonate solution ((v/v)=1/1) was added to quench reaction, the resultant was extracted with dichloromethane, washed with brine, concentrated, and purified by column chromatography (petroleum ether/ethyl acetate (v/v)=25/1) to give product 15-6 (157 mg, yield 45% in two steps). $^1$H NMR (CDCl$_3$, 300 MHz) δ4.73 (s, 2H), 4.29 (s, 1H), 2.36 (dt, J=7.8, 1.8 Hz, 1H), 2.30 (s, 3H), 2.26-1.97 (m, 3H), 1.72 (s, 6H), 1.68 (s, 6H), 1.58 (td, J=12.6, 10.2 Hz, 1H), 0.88 (s, 9H), 0.08 (s, 6H).

Compound 15-6 (1.50 g, 3.46 mmol) was dissolved in toluene (60.0 ml) and methanol (15.0 ml) and the reaction mixture was heated to an external temperature of 80° C. and refluxed overnight. The next day, the resultant was concentrated and isolated by column chromatography (petroleum ether/ethyl acetate (v/v)=10/1) to give the product 15-7 (yellow oil, 1.21 g, yield 86%). $^1$H NMR (CDCl$_3$, 300 MHz) δ4.74 (s, 2H), 3.88 (dd, J=6.0, 12.0 Hz, 1H), 3.75 (s, 3H), 2.52 (dd, J=3.0, 12.0 Hz, 1H), 2.20 (s, 3H), 2.15-1.99 (m, 3H), 1.80-1.74 (m, 1H), 1.69 (s, 3H), 1.36 (td, J=12.6, 10.2 Hz, 1H), 1.19 (s, 3H), 0.88 (s, 9H), 0.09 (s, 3H), 0.07 (s, 3H).

A solution of compound 15-7 (78.00 mg, 0.19 mmol) in THF was added dropwise to a solution of 1 M LHMDS (2.00 ml, 2.00 mmol) in THF at 0° C., and the mixture was warmed to room temperature and stirred for 4 h. Nicotinoyl chloride hydrochloride was rapidly added, and the mixture was stirred for 2 h at room temperature. When the raw material was exhausted which was monitored by TLC, the reaction was quenched by addition of acetic acid, the resultant was diluted with water, extracted with dichloromethane, dried over anhydrous sodium sulfate, concentrated. The resultant was purified by column chromatography (petroleum ether/acetone (v/v)=3/1) to give an important intermediate 15-8 as a white solid (41.00 mg, yield 45% in two steps). $^1$H NMR (CDCl$_3$, 300 MHz) δ9.06 (d, J=1.2 Hz, 1H), 8.75 (d, J=3.6 Hz, 1H), 8.19 (d, J=8.4 Hz, 1H), 7.45 (dd, J=4.8, 8.1 Hz, 1H), 6.50 (s, 1H), 4.89 (s, 2H), 4.03 (dd, J=10.8, 4.8 Hz, 1H), 2.71 (dd, J=12.3, 3.6 Hz, 1H), 2.28 (d, J=13.5 Hz, 1H), 2.13 (t, J=12.9 Hz, 1H), 1.88 (d, J=13.8 Hz, 1H), 1.76 (s, 3H), 1.44 (q, J=12.9 Hz, 1H), 1.34 (s, 3H), 1.31 to 1.23 (m, 1H), 0.96 (s, 9H), 0.07 (s, 3H), 0.04 (s, 3H).

Compound 15-8 (134 mg, 0.279 mmol) was dissolved in glacial acetic acid (7.4 ml) and water (0.03 ml). Silver acetate (100 mg, 0.594 mmol) and iodine (83 mg, 0.327 mmol) were added and the mixture was stirred overnight at room temperature. The next day, the resultant was added with water, extracted with ethyl acetate, and the organic phase was washed with brine, concentrated by rotary evaporation, and isolated by column chromatography (dichloromethane/methanol (v/v)=25/1) to give compound 15-9, which contained two isomers 15-9-a (33 mg) and 15-9-b (44 mg). 15-9-a: $^1$H NMR (CDCl$_3$, 400 MHz) δ 9.03 (d, J=2.8 Hz, 1H), 8.73 (d, J=4.8 Hz, 1H), 8.16 (dd, J=2.8, 10.4 Hz, 1H), 7.44 (dd, J=6.8, 11.2 Hz, 1H), 6.44 (s, 1H), 4.08 (dd, J=12.0, 32.0 Hz, 2H), 4.00 (dd, J=4.0, 8.0 Hz, 1H), 2.68 (dd, J=4.0, 16.0 Hz, 1H), 2.21 (d, J=16.0 Hz, 1H), 2.11 (s, 3H), 2.01 (d, J=12.0 Hz, 1H), 1.72 (t, J=12.0 Hz, 1H), 1.37 (dd, J=12.0, 24.0 Hz, 1H), 1.31 (s, 3H), 1.20 (s, 3H), 1.15 (dd, J=8.0, 24.0 Hz, 1H), 0.95 (s, 9H), 0.19 (s, 3H), 0.14 (s, 3H).

15-9-b: $^1$H NMR (CDCl$_3$, 400 MHz) δ9.05 (s, 1H), 8.75 (d, J=4.0 Hz, 1H), 8.18 (d, J=8.0 Hz, 1H), 7.45 (dd, J=4.0, 8.0 Hz, 1H), 6.43 (s, 1H), 4.07 (dd, J=12.0, 32.0 Hz, 2H), 3.98 (dd, J=4.0, 8.0 Hz, 1H), 2.66 (dd, J=4.0, 16.0 Hz, 1H), 2.36 (d, J=16.0 Hz, 1H), 2.12 (s, 3H), 1.89 (d, J=12.0 Hz, 1H), 1.70 (t, J=12.0 Hz, 1H), 1.37-1.26 (m, 2H), 1.32 (s, 3H), 1.22 (s, 3H), 0.95 (s, 9H), 0.19 (s, 3H), 0.14 (s, 3H).

Acetyl chloride (0.06 ml, 0.6 mmol) was added dropwise to 0.7 ml of methanol, and the mixture was stirred for 5 minutes at room temperature. Subsequently, a solution of compound 15-9 (33 mg, 0.060 mmol) in methanol was added and the mixture was stirred for 1 hour at room temperature. The mixture was concentrated and directly subjected to the next step. The crude product was dissolved in dichloromethane and a catalytic amount of DMAP, triethylamine (0.09 ml, 0.60 mmol) and acetic anhydride (0.04 ml, 0.30 mmol) were added and the mixture was stirred overnight at room temperature. After the reaction was complete which was monitored by TLC, the reaction was quenched with water, and the resultant was extracted with ethyl acetate, dried over anhydrous sodium sulfate, concentrated, isolated and purified by column chromatography (dichloromethane/methanol (v/v)=50/1) to give compound 15-10 as a yellow solid (yield 80%), since compounds 15-9-a and 15-9-b were isolated from 15-9 in the last step, the compounds 15-10-a, 15-10-a' and 15-10-b, 15-10-b' were obtained accordingly.

15-10-a: $^1$H NMR (CDCl$_3$, 400 MHz) δ9.11 (s, 1H), 8.79 (s, 1H), 8.22 (d, J=8.0 Hz, 1H), 7.48 (s, 1H), 6.55 (s, 1H), 5.33 (dd, J=4.0, 8.0 Hz, 1H), 4.47 (dd, J=12.0, 100.0 Hz, 2H), 2.82 (dd, J=4.0, 8.0 Hz, 1H), 2.23-1.86 (m, 3H), 2.22 (s, 3H), 2.11 (s, 3H), 2.05 (s, 3H), 1.59-1.29 (m, 2H), 1.52 (s, 3H), 1.45 (s, 3H).

15-10-a': $^1$H NMR (CDCl$_3$, 300 MHz) δ9.02 (d, J=1.8 Hz, 1H), 8.72 (d, J=4.5 Hz, 1H), 8.16 (td, J=1.5, 7.8 Hz, 1H), 7.42 (dd, J=5.1, 8.4 Hz, 1H), 6.55 (s, 1H), 5.38 (dd, J=5.1, 11.7 Hz, 1H), 4.43 (s, 2H), 2.98 (s, 1H), 2.62 (d, J=13.5 Hz, 1H), 2.50-1.12 (m, 4H), 2.30 (s, 3H), 2.23 (s, 3H), 2.14 (s, 3H), 1.66 (s, 3H), 1.49 (s, 3H).

15-10-b: $^1$H NMR (CDCl$_3$, 400 MHz) δ9.08 (s, 1H), 8.76 (d, J=4.0 Hz, 1H), 8.19 (d, J=4.0 Hz, 1H), 7.46 (dd, J=4.0, 8.0 Hz, 1H), 6.55 (s, 1H), 5.29 (dd, J=4.0, 8.0 Hz, 1H), 4.44 (dd, J=8.0, 48.0 Hz, 2H), 2.79 (dd, J=4.0, 8.0 Hz, 1H), 2.38-1.97 (m, 3H), 2.19 (s, 3H), 2.10 (s, 3H), 2.03 (s, 3H), 1.57-1.28 (m, 2H), 1.47 (s, 3H), 1.43 (s, 3H).

15-10-b': $^1$H NMR (CDCl$_3$, 300 MHz) δ9.02 (d, J=1.8 Hz, 1H), 8.72 (d, J=4.5 Hz, 1H), 8.16 (td, J=1.5, 7.8 Hz, 1H), 7.42 (dd, J=5.1, 8.4 Hz, 1H), 6.55 (s, 1H), 5.38 (dd, J=5.1, 11.7 Hz, 1H), 4.41 (dd, J=11.7, 67.2 Hz, 2H), 2.98 (s, 1H), 2.62 (d, J=13.5 Hz, 1H), 2.50-1.12 (m, 4H), 2.30 (s, 3H), 2.23 (s, 3H), 2.14 (s, 3H), 1.66 (s, 3H), 1.49 (s, 3H).

Compound 15-10 (11 mg, 0.021 mmol) (15-10-a, 15-10-a', 15-10-b, 15-10-b' respectively) and cerium(III) chloride-heptahydrate (55 mg, 0.147 mmol) were dissolved in methanol and cooled to −78° C. Sodium borohydride (5.6 mg, 0.147 mmol) was added carefully and the mixture was stirred for 30 minutes and the raw material disappeared. After the reaction was quenched with acetone, the resultant was diluted with ethyl acetate, and the organic phase was washed with water, washed with brine, dried, concentrated, isolated and purified by column chromatography (dichloromethane/methanol (v/v)=50/1) to give final product 15 as a light yellow solid (8.5 mg, yield 78%): (CDCl$_3$, 300 MHz) δ 9.01 (s, 1H), 8.69 (d, J=4.8 Hz, 1H), 8.09 (dd, J=1.8, 8.1 Hz, 1H), 7.39 (dd, J=4.8, 8.1 Hz, 1H), 6.49 (s, 1H), 5.08 (dd, J=4.8, 12.0 Hz, 1H), 4.56-4.34 (m, 4H), 2.34-1.99 (m, 2H), 2.17 (s, 3H), 2.07 (s, 3H), 1.99 (s, 3H), 1.89 (t, J=12.0 Hz, 1H), 1.58-1.51 (m, 1H), 1.48 (s, 3H), 1.30 (s, 3H), 1.13 (dd, J=13.2, 26.1 Hz, 1H).

And 16: $^1$HNMR (CDCl$_3$, 300 MHz) δ8.97 (s, 1H), 8.67 (dd, J=1.2, 4.5 Hz, 1H), 8.09 (td, J=1.8, 7.8 Hz, 1H), 7.39 (dd, J=4.8, 8.1 Hz, 1H), 6.39 (s, 1H), 5.04 (dd, J=4.8, 12.0 Hz, 1H), 4.78 (d, J=9.6 Hz, 1H), 4.45 (dd, J=12.3, 70.5 Hz, 2H), 2.59-1.24 (m, 6H), 2.22 (s, 3H), 2.08 (s, 3H), 1.92 (s, 3H), 1.63 (s, 3H), 1.50 (s, 3H).

And 17: $^1$HNMR (CDCl$_3$, 300 MHz) δ9.00 (d, J=2.1 Hz, 1H), 8.68 (dd, J=0.9, 4.5 Hz, 1H), 8.09 (td, J=1.5, 8.4 Hz, 1H), 7.40 (dd, J=4.8, 8.1 Hz, 1H), 6.49 (s, 1H), 5.06 (dd, J=5.1, 12.3 Hz, 1H), 4.52-4.32 (m, 4H), 2.39-2.23 (m, 2H), 2.16 (s, 3H), 2.03 (s, 3H), 1.99 (s, 3H), 2.02-1.85 (m, 2H), 1.54-1.15 (m, 2H), 1.48 (s, 3H), 1.24 (s, 3H).

And 18: $^1$HNMR (CDCl$_3$, 300 MHz) δ8.97 (s, 1H), 8.67 (dd, J=1.2, 4.5 Hz, 1H), 8.09 (td, J=1.8, 7.8 Hz, 1H), 7.39 (dd, J=4.8, 8.1 Hz, 1H), 6.39 (s, 1H), 5.03 (dd, J=4.8, 12.0 Hz, 1H), 4.76 (d, J=9.6 Hz, 1H), 4.51-4.34 (m, 3H), 2.59-1.24 (m, 6H), 2.19 (s, 3H), 2.11 (s, 3H), 2.03 (s, 3H), 1.56 (s, 3H), 1.49 (s, 3H).

The following compounds were synthesized in the same manner:

compound 19 was prepared by replacing the compound R-carvone in Preparation Example 6 with S-carvone;

compound 20 was prepared by replacing the compound R-carvone in Preparation Example 6 with S-carvone;

compound 21 was prepared by replacing the compound R-carvone in Preparation Example 6 with S-carvone;

compound 22 was prepared by replacing the compound R-carvone in Preparation Example 6 with S-carvone;

| Compound | Chemical structure | ¹H NMR (CDCl₃, 300 MHz) data |
|---|---|---|
| 19 | 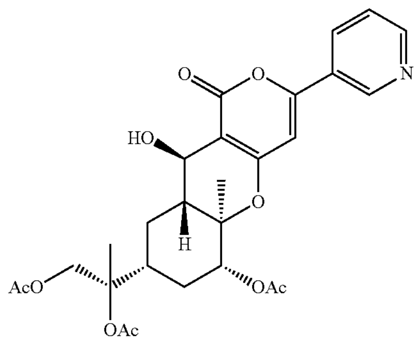 | δ 9.01 (s, 1H), 8.69 (d, J = 4.8 Hz, 1H), 8.09 (dd, J = 1.8, 8.1 Hz, 1H), 7.39 (dd, J = 4.8, 8.1 Hz, 1H), 6.49 (s, 1H), 5.08 (dd, J = 4.8, 12.0 Hz, 1H), 4.56-4.34 (m, 4H), 2.34-1.99 (m, 2H), 2.17 (s, 3H), 2.07 (s, 3H), 1.99 (s, 3H), 1.89 (t, J = 12.0 Hz, 1H), 1.58-1.51 (m, 1H), 1.48 (s, 3H), 1.30 (s, 3H), 1.13 (dd, J = 13.2, 26.1 Hz, 1H). |
| 20 | 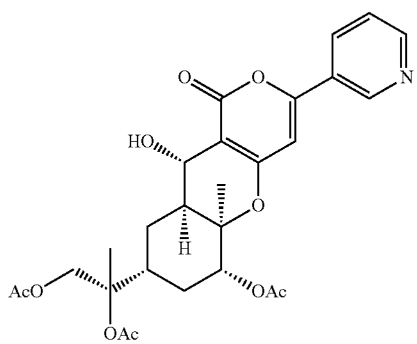 | δ 8.97 (s, 1H), 8.67 (dd, J = 1.2, 4.5 Hz, 1H), 8.09 (td, J = 1.8, 7.8 Hz, 1H), 7.39 (dd, J = 4.8, 8.1 Hz, 1H), 6.39 (s, 1H), 5.04 (dd, J = 4.8, 12.0 Hz, 1H), 4.78 (d, J = 9.6 Hz, 1H), 4.45 (dd, J = 12.3, 70.5 Hz, 2H), 2.59-1.24 (m, 6H), 2.22 (s, 3H), 2.08 (s, 3H), 1.92 (s, 3H), 1.63 (s, 3H), 1.50 (s, 3H). |
| 21 | 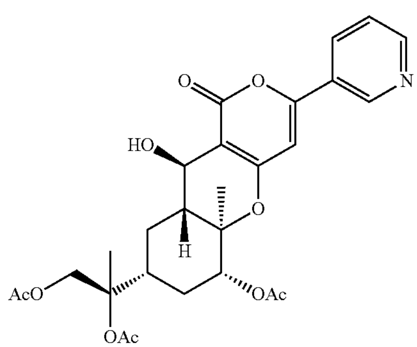 | δ 9.00 (d, J = 2.1 Hz, 1H), 8.68 (dd, J = 0.9, 4.5 Hz, 1H), 8.09 (td, J = 1.5, 8.4 Hz, 1H), 7.40 (dd, J = 4.8, 8.1 Hz, 1H), 6.49 (s, 1H), 5.06 (dd, J = 5.1, 12.3 Hz, 1H), 4.52-4.32 (m, 4H), 2.39-2.23 (m, 2H), 2.16 (s, 3H), 2.03 (s, 3H), 1.99 (s, 3H), 2.02-1.85 (m, 2H), 1.54-1.15 (m, 2H), 1.48 (s, 3H), 1.24 (s, 3H). |
| 22 | 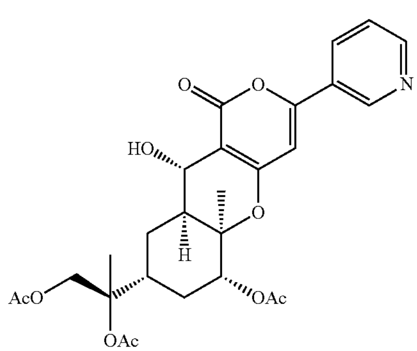 | δ 8.97 (s, 1H), 8.67 (dd, J = 1.2, 4.5 Hz, 1H), 8.09 (td, J = 1.8, 7.8 Hz, 1H), 7.39 (dd, J = 4.8, 8.1 Hz, 1H), 6.39 (s, 1H), 5.03 (dd, J = 4.8, 12.0 Hz, 1H), 4.76 (d, J = 9.6 Hz, 1H), 4.51-4.34 (m, 3H), 2.59-1.24 (m, 6H), 2.19 (s, 3H), 2.11 (s, 3H), 2.03 (s, 3H), 1.56 (s, 3H), 1.49 (s, 3H). |

Preparation Example 7 (Compound No.: ZY529I-O)

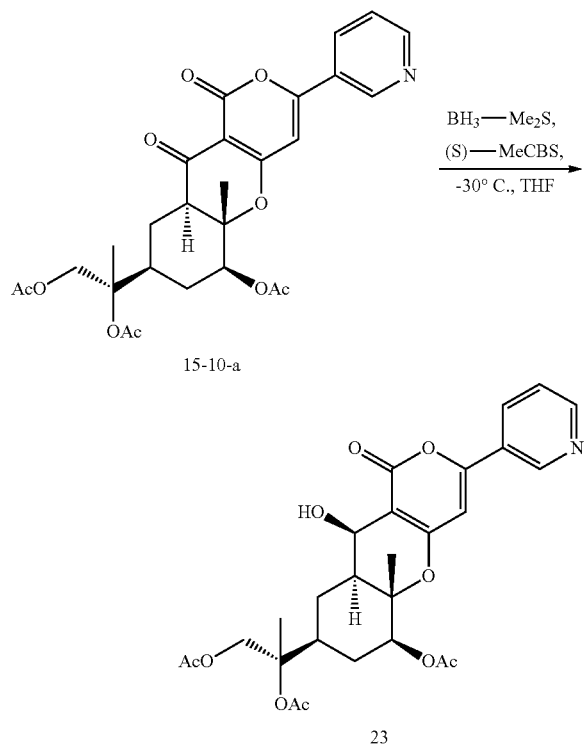

To a solution of (S)-MeCBS (5.0 mg, 0.015 mmol) in THF, $BH_3$-$Me_2S$ (0.006 ml, 0.046 mmol) was added dropwise carefully, and the mixture was stirred for 10 min at room temperature and cooled to −30° C. Then a solution of the compound 15-10-a (8.0 mg, 0.015 mmol), obtained from Preparation Example 7, in THF was further added to the resulting mixture and the mixture was stirred for 2 hours at low temperature. When the raw material was exhausted which was monitored by TLC, the reaction was quenched by addition of methanol, and the resultant was diluted with water, extracted with dichloromethane, concentrated, and isolated by column chromatography (dichloromethane/methanol (v/v)=50/1) to give product 23 (4.0 mg, yield 50%): $^1$HNMR ($CDCl_3$, 300 MHz) δ9.03 (s, 1H), 8.69 (dd, J=4.8 Hz, 1H), 8.11 (d, J=7.8 Hz, 1H), 7.40 (dd, J=4.8, 7.8 Hz, 1H), 6.49 (s, 1H), 5.04 (dd, J=3.9, 11.4 Hz, 1H), 4.65 (s, 1H), 4.48 (dd, J=12.0, 65.4 Hz, 2H), 2.82 (s, 1H), 2.41-2.37 (m, 1H) 2.10-1.56 (m, 5H), 2.18 (s, 3H), 2.10 (s, 3H), 1.92 (s, 3H), 1.50 (s, 3H), 1.49 (s, 3H).

The following compounds were synthesized in the same manner:

compound 24 was prepared by replacing the compound 15-10-a in Preparation Example 7 with 15-10-b;

compound 25 was prepared by replacing the compound 15-10-a in Preparation Example 7 with its enantiomer 19-10-a;

compound 26 was prepared by replacing the compound 15-10-a in Preparation Example 6 with 19-10-b, the enantiomer of 15-10-b.

| Compound | Chemical structure | $^1$H NMR ($CDCl_3$, 300 MHz) data |
|---|---|---|
| 24 | 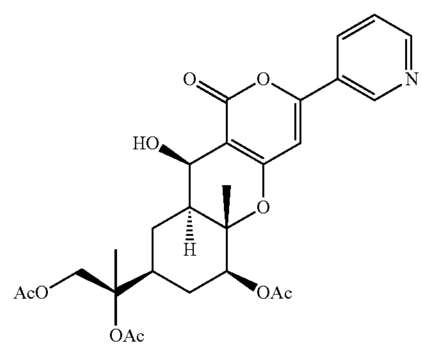 | δ 9.02 (s, 1H), 8.69 (s, 1H), 8.10 (d, J = 7.8 Hz, 1H), 7.41 (dd, J = 4.8, 8.1 Hz, 1H), 6.48 (s, 1H), 5.03 (dd, J = 4.5, 11.7 Hz, 1H), 4.65 (d, J = 3.6 Hz, 1H), 4.45 (dd, J = 12.0, 47.7 Hz, 2H), 2.92 (s, 1H), 2.92-2.41 (m, 1H), 2.03-1.30 (m, 5H), 2.16 (s, 3H), 2.09 (s, 3H), 2.03 (s, 3H), 1.50 (s, 3H, 1.48 (s, 3H). |
| 25 | 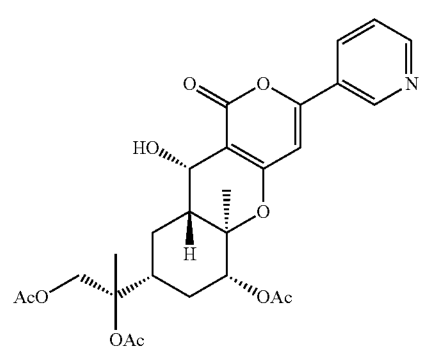 | δ 9.03 (s, 1H), 8.69 (dd, J = 4.8 Hz, 1H), 8.11 (d, J = 7.8 Hz, 1H), 7.40 (dd, J = 4.8, 7.8 Hz, 1H), 6.49 (s, 1H), 5.04 (dd, J = 3.9, 11.4 Hz, 1H), 4.65 (s, 1H), 4.48 (dd, J = 12.0, 65.4 Hz, 2H), 2.82 (s, 1H), 2.41-2.37 (m, 1H), 2.10-1.56 (m, 5H), 2.18 (s, 3H), 2.10 (s, 3H), 1.92 (s, 3H), 1.50 (s, 3H), 1.49 (s, 3H). |

| Compound | Chemical structure | ¹H NMR (CDCl₃, 300 MHz) data |
|---|---|---|
| 26 | 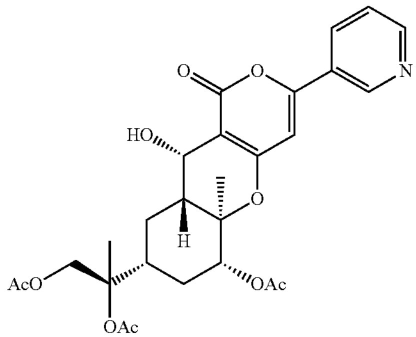 | δ 9.02 (s, 1H), 8.69 (s, 1H), 8.10 (d, J = 7.8 Hz, 1H), 7.41 (dd, J = 4.8, 8.1 Hz, 1H), 6.48 (s, 1H), 5.03 (dd, J = 4.5, 11.7 Hz, 1H), 4.65 (d, J = 3.6 Hz, 1H), 4.45 (dd, J = 12.0, 47.7 Hz, 2H), 2.92 (s, 1H), 2.92-2.41 (m, 1H), 2.03-1.30 (m, 5H), 2.16 (s, 3H), 2.09 (s, 3H), 2.03 (s, 3H), 1.50 (s, 3H), 1.48 (s, 3H). |
Preparation Example 8 (Compound No.: 28 and 29)
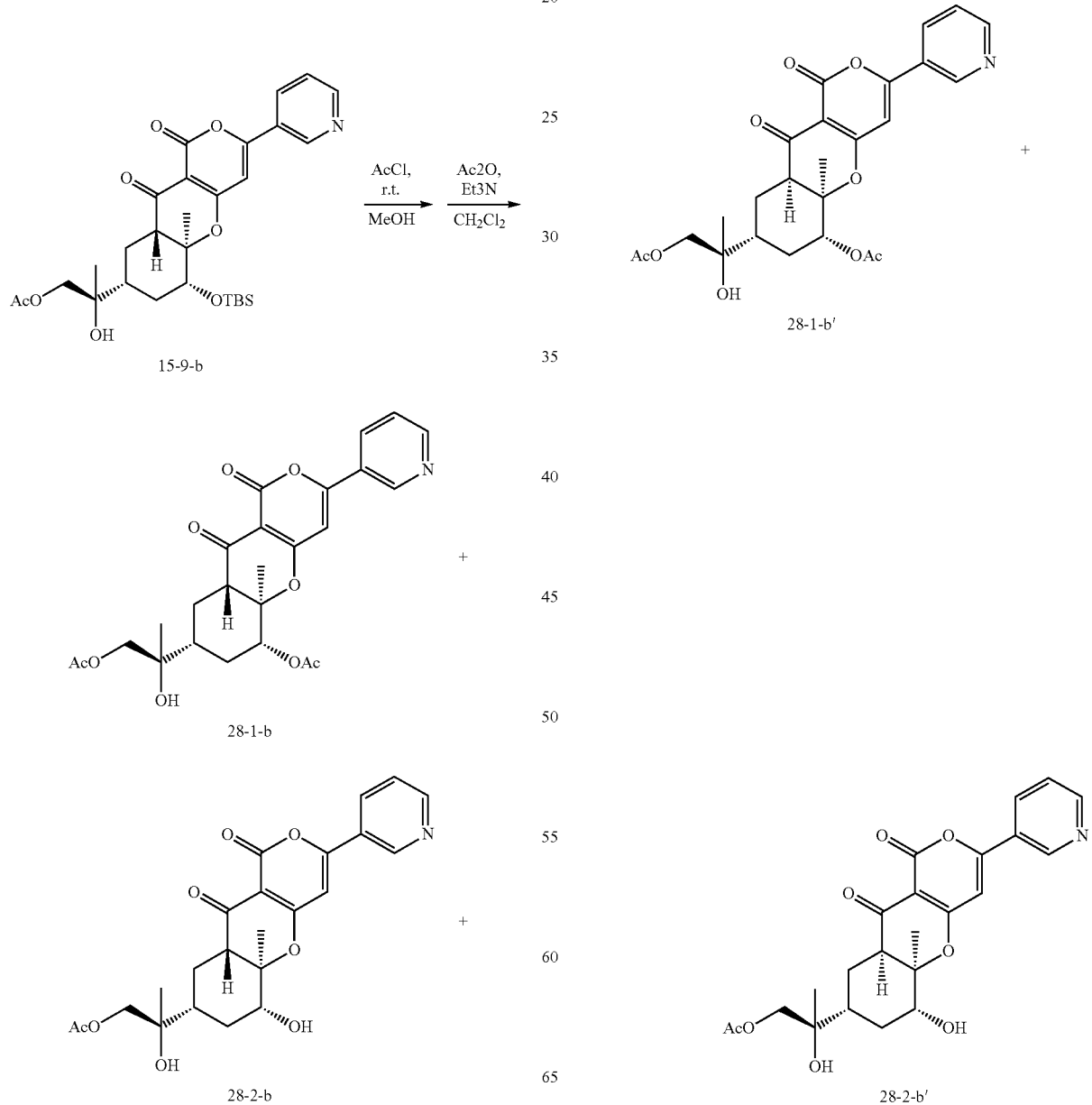

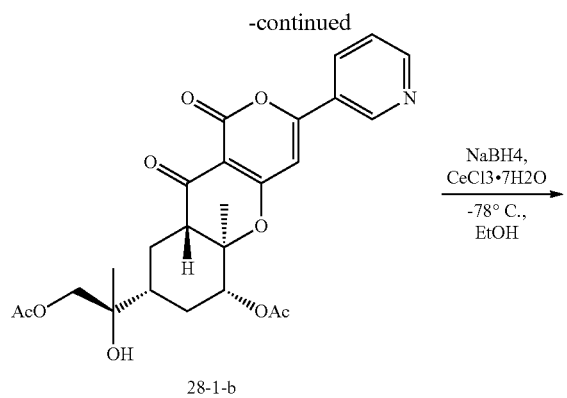

Acetyl chloride (0.20 ml, 1.83 mmol) was added dropwise to 2.5 ml of methanol, and the mixture was stirred for 5 minutes at room temperature. Subsequently, a solution of the compound 15-9-b (102.0 mg, 0.18 mmol) in methanol was added and the mixture was stirred for 1 hour at room temperature. The resultant was concentrated and directly subjected to the next step. The crude product was dissolved in dichloromethane, and triethylamine (0.28 ml, 1.83 mmol), acetic anhydride (0.13 ml, 0.92 mmol) were added. The mixture was stirred for 2 hours at room temperature. After the reaction was complete which was monitored by TLC, the reaction was quenched by addition of water, extracted with dichloromethane, concentrated, isolated and purified by column chromatography (dichloromethane/methanol (v/v)=25/1) to give a yellow solid, which is a mixture of two diastereoisomers 28-1-b and 28-1-b', and a mixture of two diastereoisomers 28-2-b and 28-2-b', including four compounds 28-1-b, 28-1-b', 28-2-b, 28-2-b' (yield 75%) in total.

The mixture of the 28-1-b and 28-1-b' and the mixture of 28-2-b and 28-2-b' were directly subjected to the next luche reduction reaction respectively, and the next reaction was carried out selectively with 28-1-b, 28-2-b, so that pure products 28 and 29 could be obtained. For example, the mixture 28-1-b and 28-1-b' (4.0 mg, 0.01 mmol in total) and cerium(III) chloride heptahydrate (22 mg, 0.058 mmol) were dissolved in anhydrous ethanol and cooled to −78° C. Sodium borohydride (3.0 mg, 0.058 mmol) was added carefully and the mixture was stirred for 30 minutes and the material disappeared. The reaction was quenched with acetone, the resultant was diluted with ethyl acetate, and the organic phase was washed with water and brine, dried, concentrated, isolated and purified by column chromatography (dichloromethane/methanol (v/v)=50/1) to give final product 28 as a light yellow solid (4.0 mg, yield 38%): $^1$HNMR (CDCl$_3$, 300 MHz) δ9.05 (s, 1H), 8.73 (s, 1H), 8.19 (d, J=7.8 Hz, 1H), 7.50 (s, 1H), 6.52 (s, 1H), 5.08 (dd, J=4.8, 11.7 Hz, 1H), 4.46 (d, J=9.9 Hz, 1H), 4.05 (dd, J=11.4, 29.7 Hz, 2H), 2.42 (d, J=13.5 Hz, 1H), 2.17 (s, 3H), 2.13 (s, 3H), 2.09-1.31 (m, 5H), 1.31 (s, 3H), 1.21 (s, 3H).

The following compound was synthesized in the same manner:

compound 29 was prepared by replacing the compound 28-1-b in Preparation Example 8 with 28-2-b.

| Compound | Chemical structure | $^1$H NMR (CDCl$_3$, 300 MHz) data |
|---|---|---|
| 29 | 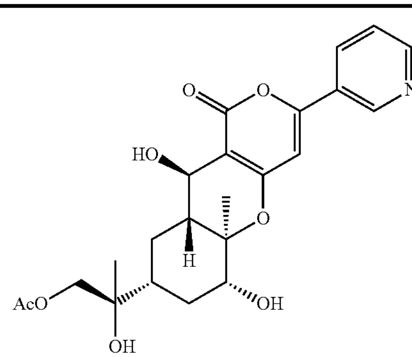 | δ 9.02 (d, J = 1.8 Hz, 1H), 8.64 (dd, J = 1.8, 5.1 Hz, 1H), 8.27 (dd, J = 4.8, 8.1 Hz, 1H), 6.87 (s, 1H), 4.41 (d, J = 9.9 Hz, 1H), 4.08 (s, 2H), 3.80 (dd, J = 4.5, 11.7 Hz, 1H), 2.32 (dd, J = 1.8, 13.2 Hz, 1H), 2.09 (s, 3H), 1.99-1.70 (m, 4H), 1.42 (dd, J = 12.3, 24.3 Hz, 1H), 1.25 (s, 3H), 1.21 (s, 3H). |

Preparation Example 9 (Compound No.: 27)

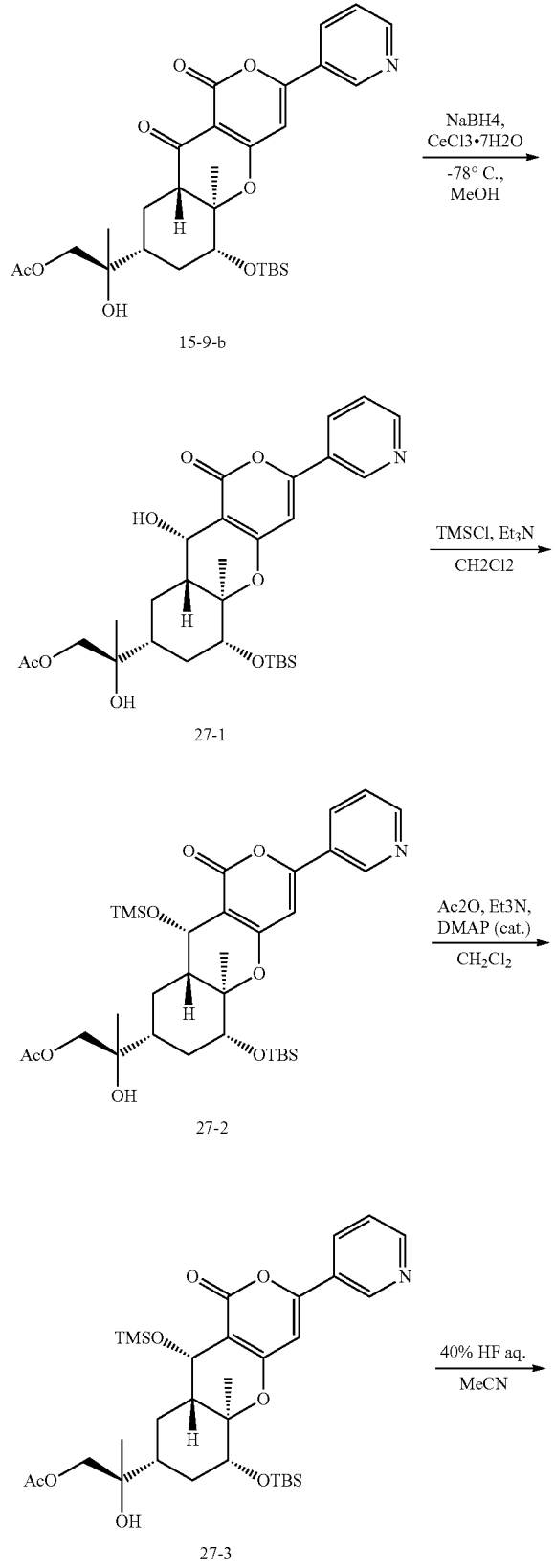

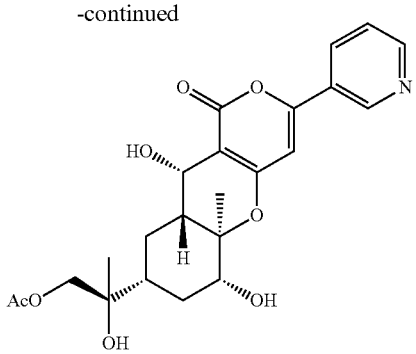

Compounds 15-9-b and cerium(III) chloride heptahydrate (96 mg, 0.173 mmol) were dissolved in methanol and cooled to −78° C. Sodium borohydride (46 mg, 1.21 mmol) was carefully added and the mixture was stirred for 30 minutes and the raw material disappeared. The reaction was quenched with acetone, and the resultant was diluted with ethyl acetate, and the organic phase was washed with water, washed with brine, dried, concentrated, isolated and purified by column chromatography (dichloromethane/methanol (v/v)=50/1) to give product 27-1 as a light yellow solid (88.0 mg, yield 92%): $^1$HNMR (CDCl$_3$, 300 MHz) δ8.96 (d, J=1.8 Hz, 1H), 8.65 (dd, J=1.8, 5.1 Hz, 1H), 8.06 (td, J=1.8, 8.1 Hz, 1H), 7.39 (td, J=0.6, 8.1 Hz, 1H), 6.35 (s, 1H), 4.45 (s, 1H), 4.42 (s, 1H), 3.99 (dd, J=11.4, 47.4 Hz, 2H), 3.75 (dd, J=4.5, 11.1 Hz, 1H), 2.42 (d, J=13.5 Hz, 1H), 2.09 (s, 3H), 1.80-1.70 (m, 3H), 1.37-1.08 (m, 2H), 1.18 (s, 3H), 0.90 (s, 9H), 0.14 (s, 3H), 0.09 (s, 3H).

Compound 27-1 (62 mg, 0.11 mmol) was dissolved in dichloromethane, and triethylamine (0.18 ml, 1.11 mmol) was added at 0° C. TMSCl (0.05 ml, 0.19 mmol) was further added and the mixture was stirred for 3.5 hours at the same temperature. The reaction was quenched with saturated sodium bicarbonate aqueous solution, and the resultant was extracted with dichloromethane, dried by rotary evaporator, and the residue was purified by column chromatography (dichloromethane/methanol (v/v)=50/1) to give product 27-2 (a white solid, yield 70%): $^1$HNMR (CDCl$_3$, 300 MHz) δ8.97 (s, 1H), 8.65 (s, 1H), 8.07 (d, J=8.1 Hz, 1H), 7.38 (t, J=4.8 Hz, 1H), 6.27 (s, 1H), 4.38 (d, J=9.3 Hz, 1H), 4.04 (dd, J=11.4, 41.1 Hz, 2H), 3.74 (dd, J=4.8, 11.7 Hz, 1H), 2.18 (d, J=13.2 Hz, 1H), 2.09 (s, 3H), 1.80-1.70 (m, 3H), 1.46-0.98 (m, 2H), 1.16 (s, 3H), 1.12 (s, 3H), 0.92 (s, 9H), 0.22 (s, 9H), 0.09 (s, 3H), 0.02 (s, 3H).

Compound 27-2 (289 mg, 0.07 mmol) was dissolved in dichloromethane, and DMAP (cat.) was added. Triethylamine (1.8 ml, 5.49 mmol) was added dropwise and acetic anhydride (1.8 ml, 5.49 mmol) was further added dropwise. The mixture was stirred for 4 hours at room temperature. The reaction was quenched with water, and the resultant was extracted with dichloromethane, concentrated and isolated by column chromatography (dichloromethane/methanol (v/v)=50/1) to give product 27-3 (127 mg, yield 42%): $^1$HNMR (CDCl$_3$, 300 MHz) δ8.99 (s, 1H), 8.67 (s, 1H), 8.08 (d, J=7.8 Hz, 1H), 7.39 (s, 1H), 6.29 (s, 1H), 4.47 (dd, J=11.4, 41.1 Hz, 2H), 4.38 (d, J=9.3 Hz, 1H), 3.74 (dd, J=4.8, 11.7 Hz, 1H), 2.37-2.15 (m, 2H), 2.09 (s, 3H), 1.96 (s, 3H), 1.84-1.76 (m, 2H), 1.42 (s, 3H), 1.39-1.25 (m, 1H), 1.20 (s, 3H), 1.11-0.94 (m, 1H), 0.86 (s, 9H), 0.20 (s, 9H), 0.11 (s, 3H), 0.06 (s, 3H).

Compound 27-3 was dissolved in acetonitrile, and 0.8 ml of 40% hydrofluoric acid solution was added. And then the mixture was stirred for 2.5 hours at room temperature. After the reaction was quenched with the saturated aqueous solution of sodium bicarbonate, the reaction solution was extracted with ethyl acetate, and the organic phase was washed with brine, concentrated, and isolated by column chromatography (dichloromethane/methanol (v/v)=25/1) to give the final product 27 (a white solid, yield 69%): $^1$HNMR (CDCl$_3$, 300 MHz) δ9.02 (s, 1H), 8.71 (s, 1H), 8.14 (d, J=7.8 Hz, 1H), 7.46 (s, 1H), 6.55 (s, 1H), 4.53-4.33 (m, 4H), 3.85 (dd, J=4.8, 11.7 Hz, 1H), 2.33 (d, J=14.1 Hz, 1H), 2.09 (s, 3H), 2.04 (s, 3H), 1.98-1.50 (m, 5H), 1.49 (s, 3H), 1.25 (s, 3H).

Preparation Example 10 (Compound No.: 30)

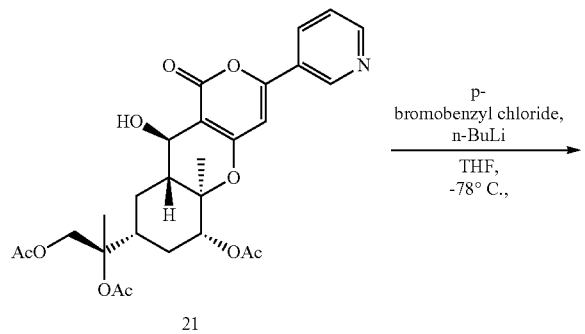

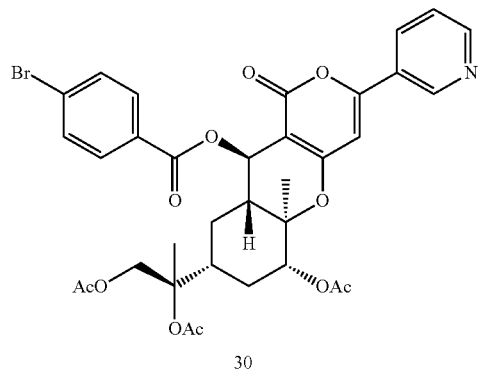

n-Butyl lithium (0.01 ml, 0.011 mmol) was added dropwise to a solution of compound 21 (6.0 mg, 0.011 mmol) in THF at −78° C., the mixture was stirred for half an hour at the same temperature, followed by the addition of p-bromobenzoyl chloride and stirring for 1 hour. After the reaction was quenched with the saturated aqueous solution of sodium bicarbonate, the reaction solution was warmed to room temperature and extracted with dichloromethane, concentrated, and isolated by column chromatography (dichloromethane/methanol (v/v)=50/1) to give product 30 (a white powder, yield 80%): $^1$HNMR (CDCl$_3$, 300 MHz) δ9.00 (s, 1H), 8.68 (d, J=5.1 Hz, 1H), 8.09 (d, J=8.4 Hz, 1H), 7.89 (d, J=8.4 Hz, 2H), 7.57 (d, J=8.4 Hz, 2H), 7.39 (dd, J=4.8, 8.1 Hz, 1H), 6.48 (s, 1H), 6.10 (d, J=10.2 Hz, 1H), 5.10 (dd, J=4.8, 11.7 Hz, 1H), 4.38 (dd, J=11.7, 48.3 Hz, 2H), 2.29-1.18 (m, 4H), 2.18 (s, 3H), 2.04 (s, 3H), 1.91 (s, 3H), 1.60-1.24 (m, 2H), 1.42 (s, 3H), 1.41 (s, 3H).

Test Example 1

Test Example for the Inhibitory Effect on ACAT2 Activity
1. Purpose:
The analogues of Pyripyropene A structure were tested for their inhibitory effect on ACAT2 activity at intact cellular level by a method in which a fluorescent-labeled sterol is used for determining ACAT2 activity.
2. Principle:
An inhibition curve was plotted based on that different concentrations of compounds would cause the fluorescence intensity to change by inhibiting the synthesis of the ester containing NBD22-fluorescent labeled sterol, thereby IC$_{50}$ was calculated.
3. Process:
HepG2 cells were cultured in a 96-well plate at a starting density of 1.5×10$^4$ cells per well for 24 hours. After the cholesterol mixture was well mixed, the cells were cultured for another 24 hours. Then NBD22-fluorescent labeled sterol at a final concentration of 0.5 μg/ml, and compounds at a final concentration gradient of 0, 0.008, 0.04, 0.2, 1 and 5 μM were added. Three wells were set for each concentration. After incubating for 6 hours, the fluorescence intensity was measured using a fluorescence analyzer (E488, A535). The fluorescence intensity values were plotted against different concentrations of the compounds and IC$_{50}$ was obtained.
4. Results: (the results are exemplified by fourteen compounds, including compounds 7, 8, 13, 21, etc., but not limited to these compounds)

TABLE 1

The inhibitory effect of the compounds on ACAT2 activity

| Compound No. | IC$_{50}$ (μM) or inhibition rate % |
| --- | --- |
| Pyripyropene A | 0.179 |
| 2 | 104% |
| 3 | 90% |
| 6 | 90% |
| 7 | 0.152 |
| 8 | 0.086 |
| 13 | 0.023 |
| 14 | 0.103 |
| 15 | 0.831 |
| 16 | 0.245 |
| 21 | 0.078 |
| 22 | 0.086 |
| 26 | 0.433 |
| 27 | 0.069 |
| 29 | 0.081 |

Note: IC$_{50}$ is a 50% inhibition evaluation of the compound samples on ACAT2 activity. Inhibition rate (%) is a relative inhibition rate with Pyripyropene A (0.2 μM) as the 100% inhibition control.

The results showed that these compounds have ACAT2 inhibition activity, and when compared with Pyripyropene A, the only ACAT2 specific inhibitor that has been found, the inhibition activity of these ACAT2 inhibitors is significantly higher.

Test Example 2

Test Example for the Selectivity Coefficient of the Inhibitory Effect on ACAT2 Activity
1. Purpose
The analogues of Pyripyropene A structure were tested for their ACAT2 and ACAT1 inhibitory effects at intact cell level by using a cholesterol oxidase method for testing ACAT activity, thereby obtaining the compounds having high ACAT2 selectivity.

2. Principle

HepG2 cells were used for testing the inhibitory effect of compounds at different concentrations on ACAT1 or ACAT2 activity, thereby obtaining $IC_{50}$ to calculate $SI(ACAT1\text{-}IC_{50}/ACAT2\text{-}IC_{50})$.

3. Process

HepG2 cells were cultured in a 6-well plate at a starting density of $4 \times 10^5$ cells per well for 24 hours, then the medium was replaced and 10 μg/ml of cholesterol and the compounds at different concentrations were added. The cells were cultured for another 9 hours and cholesterol amounts of the cells were measured with Cholesterol Assay kit.

4. Results: (the results are exemplified by 6 compounds, including compounds 7, 8, 13, 14, 21 and 22, etc., but not limited to these compounds)

TABLE 2

Selective inhibition of the compounds on ACAT2 activity

| Compound No. | ACAT1-$IC_{50}$(μM) | ACAT2-$IC_{50}$(μM) | SI |
|---|---|---|---|
| 7 | 107.7 | 0.147 | 733 |
| 8 | 64.71 | 0.061 | 1076 |
| 13 | 17.77 | 0.012 | 1496 |
| 14 | 153.7 | 0.129 | 1191 |
| 21 | 56.66 | 0.055 | 1035 |
| 22 | 87.35 | 0.090 | 971 |

The results showed that these compounds have high ACAT2-selected inhibitory activities (SI>733, HepG2 cell), which are much higher than that of Pyripyropene A (SI>200, AC29 CHO cell).

The invention claimed is:

1. Analogues of Pyripyropene A, which are represented by the following formula (I):

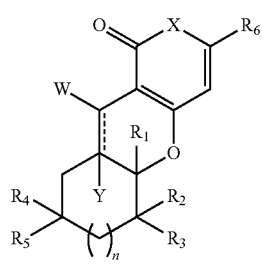

wherein:
n=0, 1 or 2;
$R_1$ is hydrogen or C1 to C6 alkyl;
$R_2$ and $R_3$ are each independently hydrogen, hydroxy, C1 to C6 alkylcarbonyloxy group, C1 to C6 alkylcarbonylthio group, C1 to C6 alkylcarbonylamine group, 3- to 8-membered cycloalkylcarbonyloxy group, 3- to 8-membered cycloalkylcarbonylthio group, 3- to 8-membered cycloalkylcarbonylamine group, substituted or unsubstituted 5- to 8-membered arylcarbonyloxy group, or substituted or unsubstituted heteroarylcarbonyloxy group, wherein the term of "substituted" means to be substituted with halogen, hydroxy, alkyl, alkoxy, amino, cyano, wherein one of $R_2$ and $R_3$ is hydrogen and the other is selected from hydroxy, acetoxy or para-cyano-substituted phenylcarbonyloxy groups;
$R_4$ and $R_5$ are each independently hydrogen, wherein one of $R_4$ and $R_5$ is hydrogen and the other is selected from

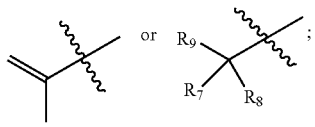

wherein $R_7$, $R_8$ and $R_9$ are each independently hydrogen, hydroxy, halogen, methyl, C1 to C6 alkylcarbonyloxy group, C1 to C6 alkylcarbonylthio group, C1 to C6 alkylcarbonylamine group, 3- to 8-membered cycloalkylcarbonyloxy group, 3- to 8-membered cycloalkylcarbonylthio group, 3- to 8-membered cycloalkylcarbonylamine group, C1 to C6 alkylcarbonyloxy methylene group, 3- to 8-membered cycloalkylcarbonyloxy methylene group, substituted or unsubstituted 5- to 8-membered heteroarylcarbonyloxy group, substituted or unsubstituted 5- to 8-membered heteroarylcarbonyloxy methylene group, substituted or unsubstituted 5- to 8-membered arylcarbonyloxy group, substituted or unsubstituted 5- to 8-membered arylcarbonyloxy methylene group, wherein the term of "substituted" means to be substituted with halogen, hydroxy, alkyl, alkoxy, amino, cyano;
$R_6$ is substituted or unsubstituted 5- to 8-membered heteroaryl;
X is an oxygen atom, a sulfur atom, an amino group or a C1 to C6 alkyl;
Y is hydrogen;
W is halogen, oxo (=O), =N—OH, substituted or unsubstituted 5- to 8-membered aryl or heteroarylcarbonyloxy group, C1 to C6 alkylcarbonyloxy group or 3- to 8-membered cycloalkylcarbonyloxy group;
==== represents a single bond or a double bond.

2. The analogues of Pyripyropene A according to claim 1, wherein
n=1;
$R_1$ is hydrogen or methyl;
$R_2$ and $R_3$ are each independently hydrogen, hydroxy, acetoxy or para-cyano-substituted phenylcarbonyloxy group, wherein one of $R_2$ and $R_3$ is hydrogen and the other is selected from hydroxyl, acetoxy or para-cyano-substituted phenylcarbonyloxy groups;
$R_4$ and $R_5$ are each independently hydrogen, wherein one of $R_4$ and $R_5$ is hydrogen and the other is selected from

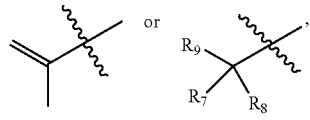

$R_7$, $R_8$ and $R_9$ are each independently hydrogen, hydroxy, halogen, methyl, C1 to C6 alkylcarbonyloxy group, substituted or unsubstituted phenylcarbonyloxy group, wherein said substitution means to be substituted with halogen, hydroxy, alkyl, alkoxy, amino, cyano;
$R_6$ is substituted or unsubstituted 5- to 8-membered heteroaryl;
X is an oxygen atom;
Y is hydrogen;
W is halogen, oxo (=O), =N—OH, substituted or unsubstituted 5- to 8-membered aryl or heteroarylcarbonyloxy group, C1 to C6 alkylcarbonyloxy group or 3- to 8-membered cycloalkylcarbonyloxy group;
==== represents a single bond or a double bond.

3. The analogues of Pyripyropene A according to claim 1, wherein n=1;

$R_1$ is methyl;

$R_2$ and $R_3$ are each independently hydrogen, hydroxy, acetoxy or para-cyano-substituted phenylcarbonyloxy group, wherein one of $R_2$ and $R_3$ is hydrogen and the other is selected from hydroxyl, acetoxy or para-cyano-substituted phenylcarbonyloxy groups;

$R_4$ and $R_5$ are each independently hydrogen, wherein one of $R_4$ and $R_5$ is hydrogen and the other is selected from

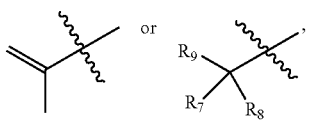

$R_7$, $R_8$ and $R_9$ are each independently hydrogen, hydroxy, halogen, methyl, C1 to C6 alkylcarbonyloxy group, substituted or unsubstituted phenylcarbonyloxy group, wherein the term of "substituted" means to be substituted with cyano;

$R_6$ is substituted or unsubstituted 5- to 8-membered heteroaryl;

X is an oxygen atom, a sulfur atom, an amino group or a C1 to C6 alkyl;

Y is hydrogen;

W is oxo (=O) or para-halogen-substituted phenylcarbonyloxy;

≈≈≈ is a single bond.

4. The analogues of Pyripyropene A according to claim 1, wherein Y is hydrogen, n=1, X is oxygen, $R_1$ is methyl, ≈≈≈ is a single bond, $R_3$ and $R_5$ are hydrogen, and the configurations of W and Y are the same, the configurations of $R_2$, $R_4$ and $R_1$ are the absolute steric configurations represented by the following formula (IV):

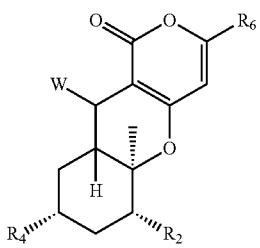

IV wherein in formula (IV), the definitions of other substituents are the same as those in formula (I) of claim 1.

5. The analogues of Pyripyropene A according to claim 1, which are selected from the following compounds:

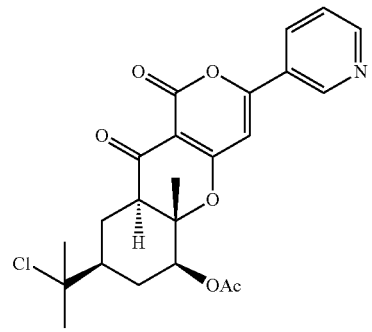

1

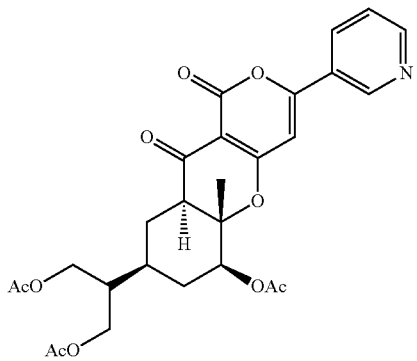

2

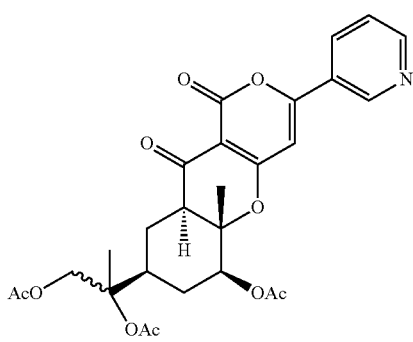

3

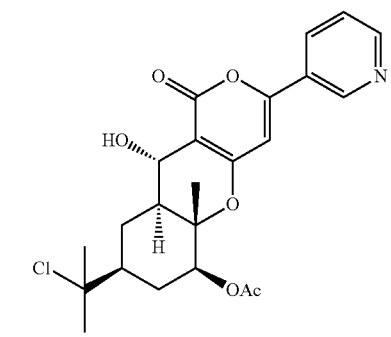

4

-continued
5
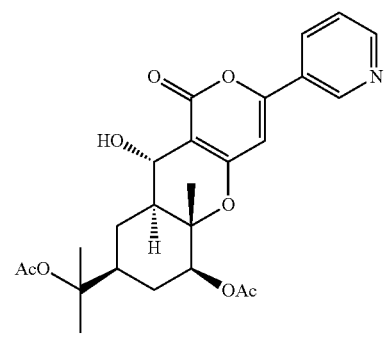
6
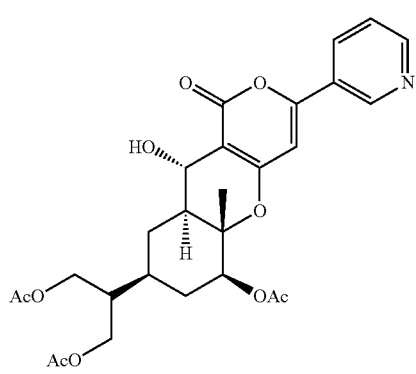
7
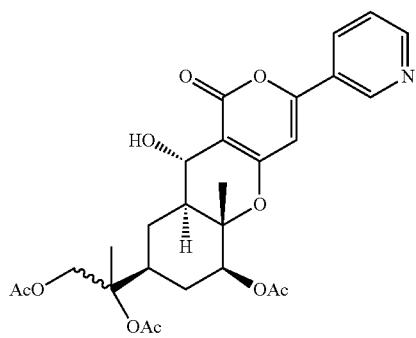
8
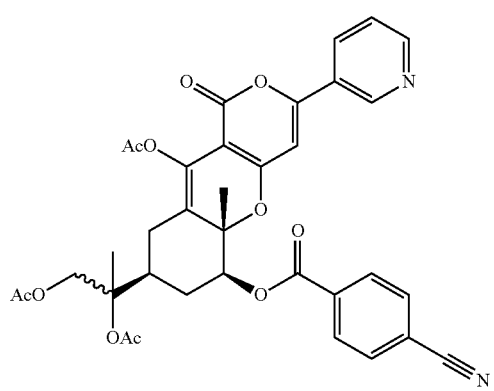
-continued
9
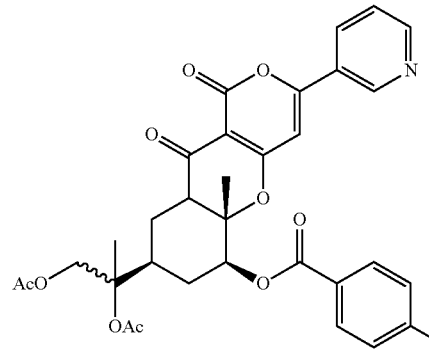
10
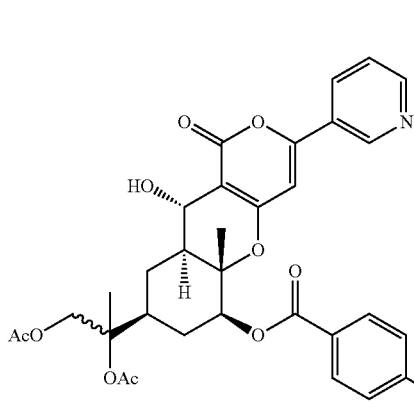
11
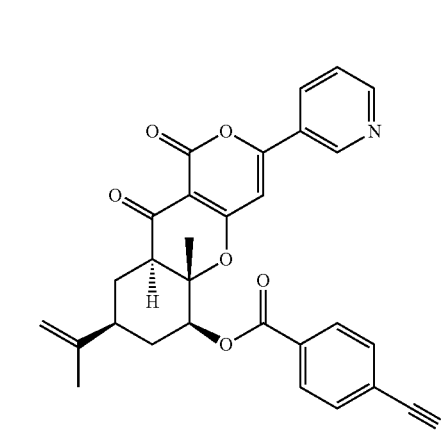
12
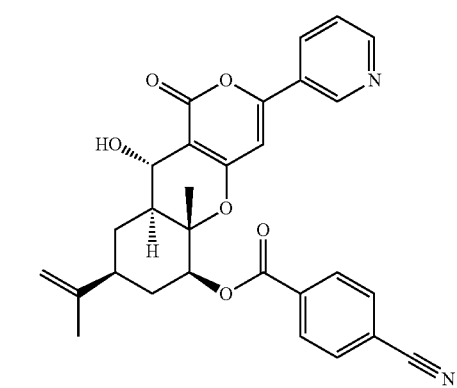

13
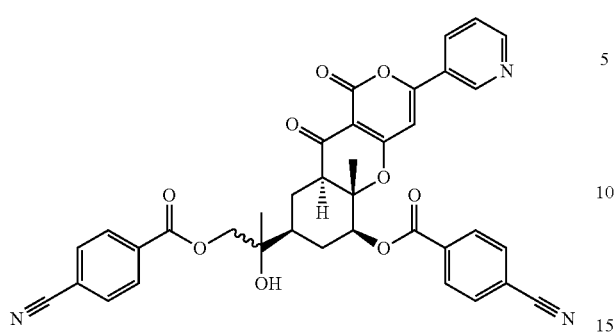
14
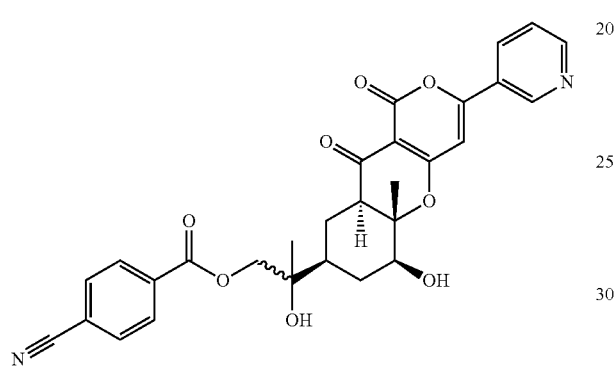
15
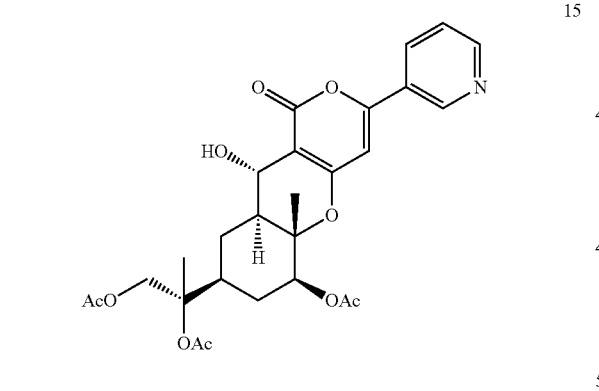
16
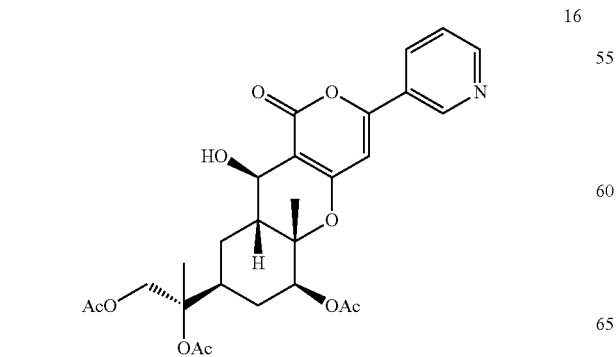
17
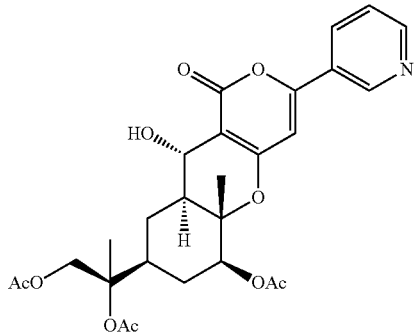
18
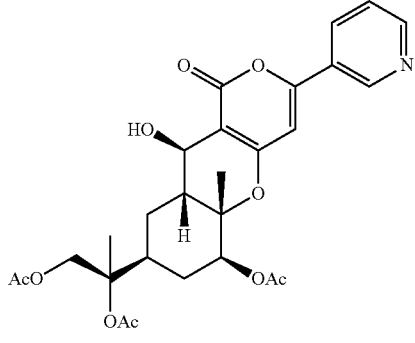
19
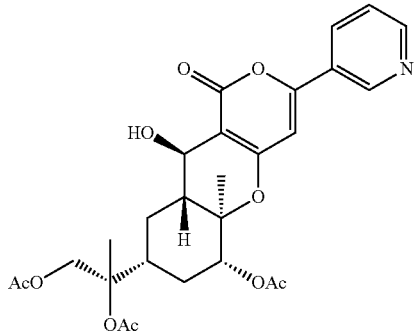
20

65
-continued
21
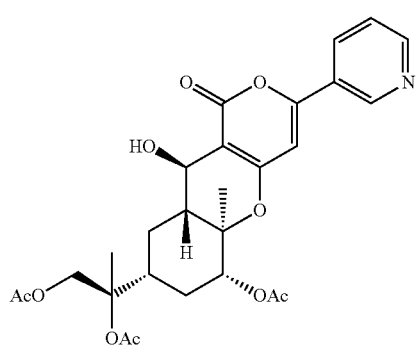
22
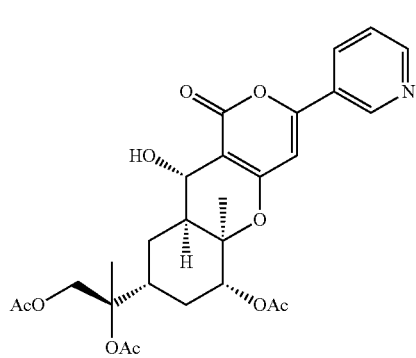
23
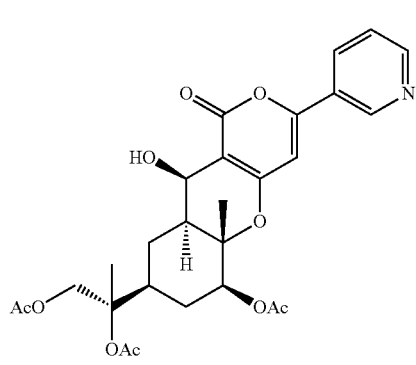
24
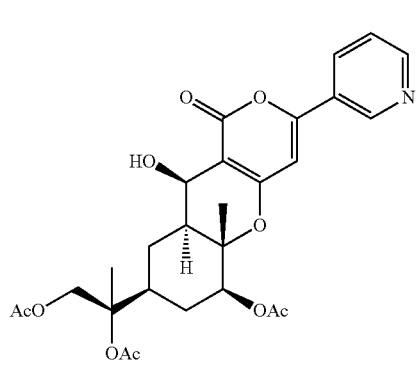
66
-continued
25
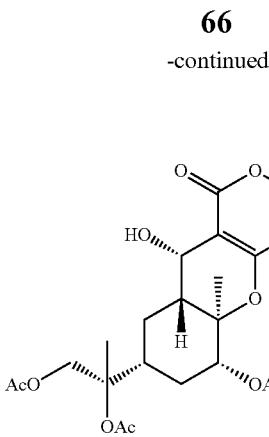
26
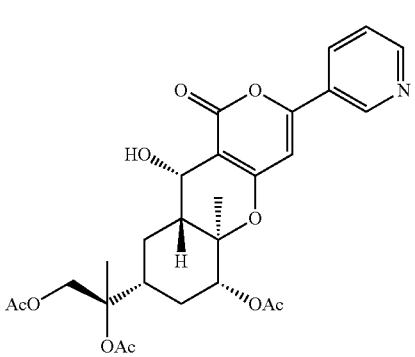
27
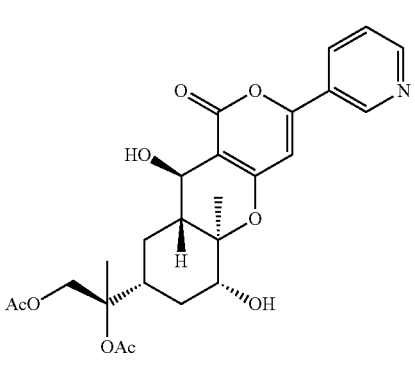
28
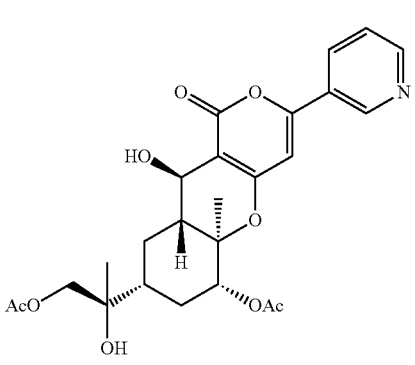

-continued
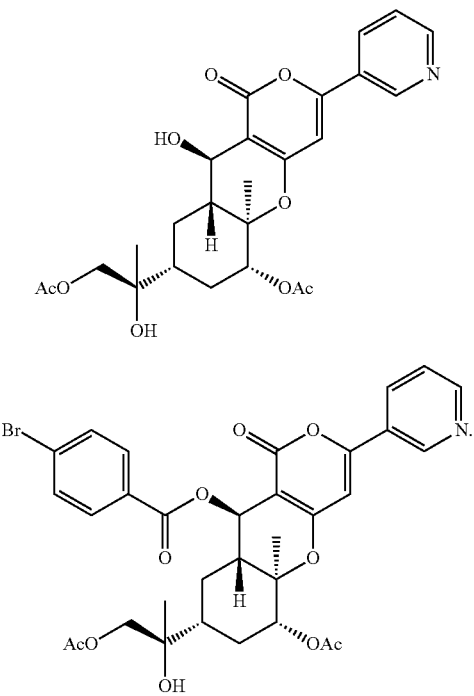
6. The analogues of Pyripyropene A according to claim 1, wherein one of $R_2$ and $R_3$ is hydrogen and the other is selected from hydroxy, acetoxy or para-cyano-substituted phenylcarbonyloxy groups;
one of $R_4$ and $R_5$ is hydrogen and the other is
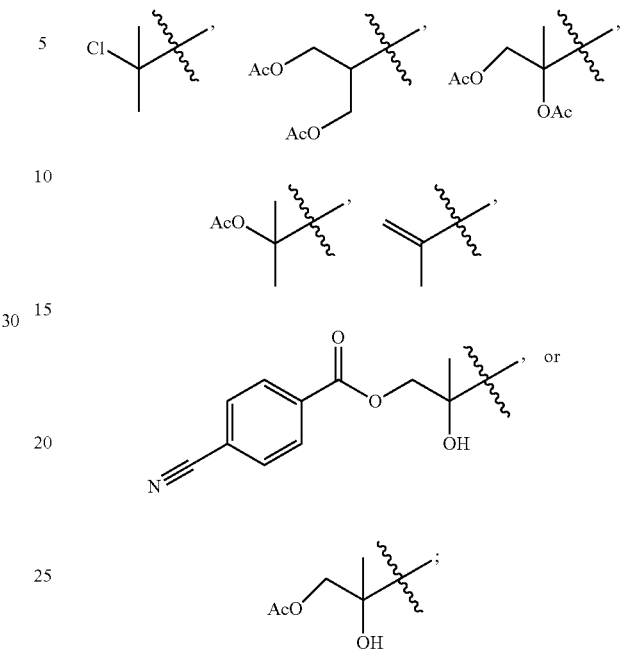
$R_6$ is a 3-pyridyl group;
X an oxygen atom.
* * * * *